(12) United States Patent
Desir

(10) Patent No.: US 11,124,779 B2
(45) Date of Patent: Sep. 21, 2021

(54) COMPOSITIONS AND METHODS FOR TREATING AND PREVENTING PANCREATITIS, RENAL INJURY AND CANCER

(71) Applicant: Yale University, New Haven, CT (US)

(72) Inventor: Gary Desir, Woodbridge, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/454,223

(22) Filed: Jun. 27, 2019

(65) Prior Publication Data

US 2019/0382736 A1 Dec. 19, 2019

Related U.S. Application Data

(63) Continuation of application No. 15/311,689, filed as application No. PCT/US2015/030980 on May 15, 2015, now abandoned.

(60) Provisional application No. 61/994,279, filed on May 16, 2014.

(51) Int. Cl.
| | |
|---|---|
| *C12N 9/00* | (2006.01) |
| *C12N 9/02* | (2006.01) |
| *C12N 15/113* | (2010.01) |
| *C12Q 1/26* | (2006.01) |
| *A61K 38/00* | (2006.01) |

(52) U.S. Cl.
CPC ........ *C12N 9/0036* (2013.01); *C12N 15/1137* (2013.01); *C12Q 1/26* (2013.01); *C12Y 106/03* (2013.01); *C12Y 306/03008* (2013.01); *A61K 38/00* (2013.01); *C12N 2310/14* (2013.01); *G01N 2333/90209* (2013.01); *G01N 2800/06* (2013.01)

(58) Field of Classification Search
None
See application file for complete search history.

(56) References Cited

U.S. PATENT DOCUMENTS

| 6,156,501 A | 12/2000 | McGall |
| 7,700,095 B2 | 4/2010 | Xu |

FOREIGN PATENT DOCUMENTS

| JP | 2001031577 A | 2/2001 |
| KR | 1020070000249 | 1/2007 |
| WO | 2008091408 | 7/2008 |
| WO | 2014014899 A | 1/2014 |
| WO | 2015200790 | 12/2015 |

OTHER PUBLICATIONS

Kolodecik et al. 2017; The serum protein renalase reduces injury in experimental pancreatitis. J. Bio. Chem. 292(51): 21047-21059.*
Hyun et al. 2014; Experimental models of pancreatitis. Clin. Endosc. 47: 212-216.*
Reed et al. May 2014; Renalase deficiency worsens acute pancreatitis in mice. Gastroenterology. 146.5, Suppl. 1:S496.*
Antalffy et al., 2012, "Plasma membrane calcium pump (PMCA) isoform 4 is targeted to the apical membrane by the w-splice insert from PMCA2." Cell Calcium 51, 171-178.
Awla et al., 2012, "NFATc3 Regulates Trypsinogen Activation, Neutrophil Recruitment, and Tissue Damage in Acute Pancreatitis in Mice." Gastroenterology 143, 1352-1360 e1357.
Barrett et al., 2009, "Genome-wide association study and meta-analysis finds over 40 loci affect risk of type 1 diabetes." Nat. Genet. 41:703-707.
Beaupre et al., 2013, "Renalase Is an a-NAD(P)H Oxidase/Anomerase." J. Am. Chem. Soc. 135:13980-13987.
Buraczynska et al., 2011, "Renalase Gene Polymorphisms in Patients With Type 2 Diabetes, Hypertension and Stroke." Neuromolecular Med. 13:321-327.
Criddle et al., 2006, "Fatty Acid Ethyl Esters Cause Pancreatic Calcium Toxicity via Inositol Trisphosphate Receptors and Loss of ATP Synthesis." Gastroenterology 130, 781-793.
Desir et al, 'Renalase Lowers Ambulatory Blood Pressure by Metabolizing Circulating Adrenaline,' 2012, J. of the Am. Heart Assn, 1(4):e002634. 11 pages.
Desir et al., 2012, 'Human renalase: a review of its biology, function, and implications for hypertension' J. Am. Soc Hypertension, 6:417-426.
European Search Report issued in corresponding European Patent Application No. 15793053.8, dated Dec. 17, 2018 (8 pages).
Falchetto et al., 1992, "The calmodulin-binding site of the plasma membrant Ca2+ pump interacts with the transduction domain of the enzyme." Protein Sci 1, 1613-1621.
Farzaneh-Far et al., 2010, 'A Functional Polymorphism in Renalase (Glu37Asp) Is Associated with Cardiac Hypertrophy, Dysfunction, and Ischemia: Data from the Heart and Soul Study.' PLoS One. 5(10):e13496.
Ferdek et al., 2012, "A Novel Role for Bcl-2 in Regulation of Cellular Calcium Extrusion." Curr Biol 22, 1241-1246.
Genbank Sequence: AK002080, 2008, *Homo sapiens* cDNA FLJ11218 fis, clone PLACE1008095, (3 pages).
Gerasimenko et al., 2002, "Menadione-induced apoptosis: roles of cytosolic Ca2+ elevations and the Mitochondrial permeability transition pore." J Cell Sci 115,485-497.
Golay et al., 2012, "Acute Pancreatitis in Chronic Kidney Disease-A Common but Often Misunderstood Combination." Ren Fail 34, 1338-1340.
Huang et al., 2014, "Fatty acid ethyl ester synthase inhibition ameliorates ethanol-induced Ca2+-dependent Titochondrial dysfunction and acute pancreatitis." Gut, 63(8):1313-24.
James et al., 1989, "Primary Structure of the cAMP-Dependent Phosphorylation Site of the Plasma Membrane Calcium Pump." Biochemistry 28, 4253-4258.

(Continued)

*Primary Examiner* — Karen Cochrane Carlson
(74) *Attorney, Agent, or Firm* — Riverside Law LLP

(57) ABSTRACT

The present invention includes compositions and methods for detecting, treating and preventing renal and pancreatic diseases and disorders.

3 Claims, 15 Drawing Sheets

Specification includes a Sequence Listing.

(56) References Cited

OTHER PUBLICATIONS

Japanese Office Action (with English language translation) for Appl. No. 2016-568038, dated Apr. 9, 2019, 10 pages.
Kes et al., 1996, "Acute Renal Failure Complicating Severe Acute Pancreatitis." Ren Fail 18, 621-628.
Lankisch et al., 2008, "Frequency and severity of acute pancreatitis in chronic dialysis patients." Nephrol Dial Transplant 23, 1401-1405.
Lee et al., 'Renalase Protects against Ischemic AKI,' 2013, J Am Soc Nephrol, 24:445-455.
Lerch et al, 1994, "Origin and development of exocrine pancreatic insufficiency in experimental renal failure." Gut 35, 401-407.
Li et al., 'Catecholamines regulate the activity, secretion, and synthesis of renalase,' 2008, Circulation, 117:1277-1282.
Lopreiato et al., 2014, "The Plasma Membrane Calcium Pump: New Ways to Look at an Old Enzyme." J Biol Chem 289, 10261-10268.
Malyszko et al., 2012, "Renalase, Stroke, and Hypertension in Hemodialyzed Patients." Ren. Fail. 34:727-731.
Mankad et al., 2012, "Insulin Protects Pancreatic Acinar Cells from Cytosolic Calcium Overload and Inhibition of Plasma Membrane Calcium Pump." J Biol Chem 287, 1823-1836.
Matozaki et al., 1990, "Two Functionally Distinct Cholecystokinin Receptors Show Different Modes of Actions on Za2+ Mobilization and Phospholipid Hydrolysis in Isolated Rat Pancreatic Acini." J Biol Chem 265, 6247-6254.
McKay et al., 2004, "The continuing challenge of early mortality in acute pancreatitis." The British journal of surgery 91, 1243-1244.
Milani et al., 'FAD-binding site and NADP reactivity in human renalase: a new enzyme involved in blood pressure regulation,' 2011, J Mol Biol, 411:463-473.
Mounzer et al., 2012, "Comparison of Existing Clinical Scoring Systems to Predict Persistent Organ Failure in Patients With Acute Pancreatitis." Gastroenterology 142, 1476-1482.
Muallem et al., 1988, "Role of Na+/Ca2+ and the Plasma Membrane Ca2+ Pump in Hormone-Mediated Ca2+ Efflux from Pancreatic Acini." J Membr Biol 102, 153-162.
Muallem et al., 1995, "Actin Filament Disassembly Is a Sufficient Final Trigger for Exocytosis in Nonexcitable Cells." J Cell Biol 128, 589-598.
Muddana et al., 2009, "Elevated Serum Creatinine as a Marker of Pancreatic Necrosis in Acute Pancreatitis." The American journal of gastroenterology 104, 164-170.
Office Action dated Feb. 8, 2019 for U.S. Appl. No. 15/311,689 (pp. 1-8).
Office Action dated Jun. 18, 2018 for U.S. Appl. No. 15/311,689 (pp. 1-8).
Pande et al., 2008, "Functional effects of caloxin 1 c2, a novel engineered selective inhibitor of plasma membrane Ca2+-pump isoform 4, on coronary artery." J. Cell. Mol. Med. 12:1049-1060.
Petersen, 2003, "Localization and regulation of Ca2+ entry and exit pathways in exocrine gland cells." Cell Calcium 33, 337-344.
Petrov et al., 2010, "Organ Failure and Infection of Pancreatic Necrosis as Determinants of Mortality in Patients With Acute Pancreatitis." Gastroenterology 139, 813-820.
Pitchumoni et al., 1996, "Acute Pancreatitis in Chronic Renal Failure." The American journal of gastroenterology 91, 2477-2482.
Quraishi et al., 2005, "Acute Pancreatitis in Patients on Chronic Peritoneal Dialysis: An Increased Risk?" The American journal of gastroenterology 100, 2288-2293.
Raraty et al, 2000, "Calcium-dependent enzyme activation and vacuole formation in the apical granular region of Pancreatic acinar cells." Proc Natl Acad Sci U S A 97, 13126-13131.
Roux et al., 2004, "ERK and p38 MAPK-Activated Protein Kinases: a Family of Protein Kinases with Diverse Biological Functions." Microbiol. Mol. Biol. Rev. 68:320-344.
Rutsky et al., 1986, "Acute Pancreatitis in Patients With End-Stage Renal Disease Without Transplantation." Archives of internal medicine 146, 1741-1745.
Samad et al., 2014, "Insulin Protects Pancreatic Acinar Cells from Palmitoleic Acid-induced Cellular Injury." J Biol Chem 289, 23582-23595.
Smallwood et al., 1988, "Regulation of Erythrocyte Ca2+ Pump Activity by Protein Kinase C." J Biol Chem 263, 2195-2202.
Strehler et al., 2013, "Plasma Membrane Calcium ATPases as Novel Candidates for Therapeutic Agent Development." Journal of pharmacy & pharmaceutical sciences: a publication of the Canadian Society for Pharmaceutical Sciences, Societe canadienne des sciences pharmaceutiques 16, 190-206.
Szewezyk et al., "Caloxins: a novel class of selective plasma membrane Ca2+ pump inhibitors obtained using biotechnlogy", Eur J. Physiol, 2008, vol. 456, p. 255-266.
Tepikin et al., 1992, "Pulsatile Ca2+ Extrusion from Single Pancreatic Acinar Cells during Receptor-activated Cytosolic Ca2+ Spiking." J Biol Chem 267, 3569-3572.
Iran et al, 1993, "Acute renal failure in patients with acute pancreatitis: prevalence, risk factors, and outcome." Nephrol Dial Transplant 8, 1079-1084.
Varga, et al., "Histone deacetylase inhibitor- and PMA-induced upregulation of PMCA4b enhances Ca2+ clearance from MCF-7 breast cancer cells," Cell Calcium, 55(20):78-92.
Wang et al., 1991, "Protein Kinase C Phosphorylates the Carboxyl Terminus of the Plasma Membrane Ca2+-ATPase from Human Erythrocytes." J Biol Chem 266, 9078-9085.
Wang et al., 2014, "Renalase Prevents AKI Independent of Amine Oxidase Activity", J. Am. Soc. Nephrol. 25:1226-1235.
Wang et al., 2015, 'Identification of a Receptor for Extracellular Renalase.' PLoS ONE. 10(4):e0122932 (13 pages).
WHITCOMB, 2006, "Acute Pancreatitis." N Engl J Med 354, 2142-2150.
Williams, 2001, "Intracellular Signaling Mechanisms Activated by Cholecystokinin-Regulating Synthesis and Secretion of Digestive Enzymes in Pancreatic Acinar Cells." Annu Rev Physiol 63, 77-97.
Wu et al., 'Renalase deficiency aggravates ischemic myocardial damage,' 2011, Kidney Int, 79: 853-860.
Wu et al., 2011, "Blood Urea Nitrogen in the Early Assessment of Acute Pancreatitis." Archives of internal medicine 171, 669-676.
Wu et al., 2013, "Clinical Management of Patients With Acute Pancreatitis." Gastroenterology 144, 1272-1281.
Xu et al., 'Renalase is a novel, soluble monoamine oxidase that regulates cardiac function and blood pressure,' 2005, J Clin Invest, 115: 1275-1280.
Zhao et al., 2007, "Renalase gene is a novel susceptibility gene for essential hypertension: a two-stage association study in northern Han Chinese population." J. Mol. Med. (Berl). 85:877-885.

* cited by examiner

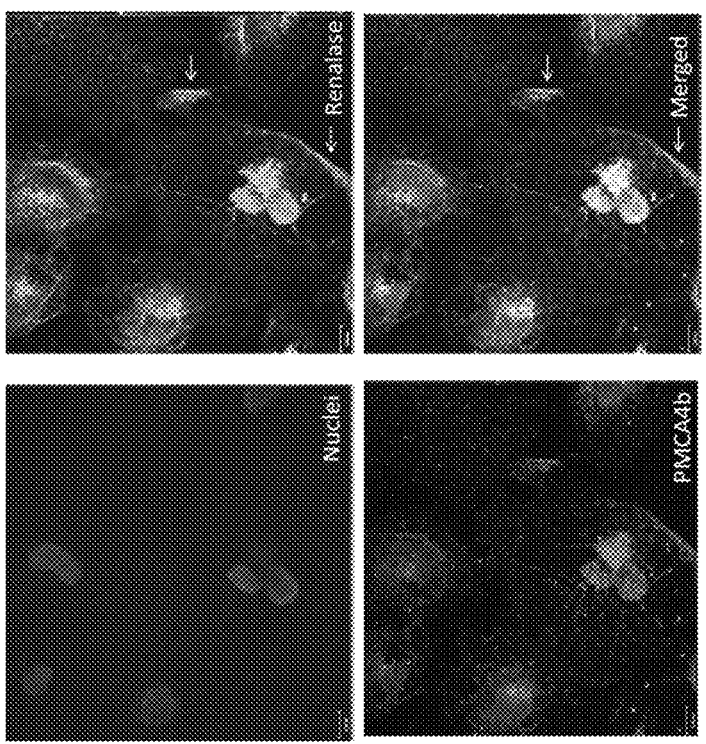
Fig. 4C
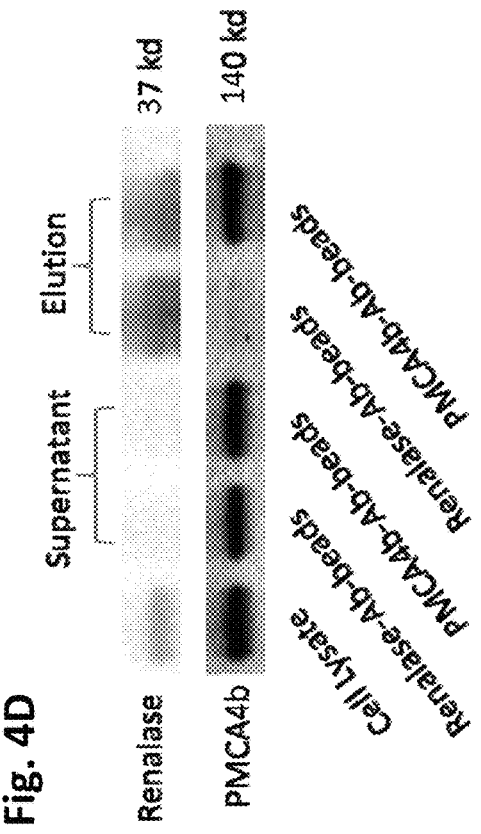
Fig. 4B
Fig. 4D

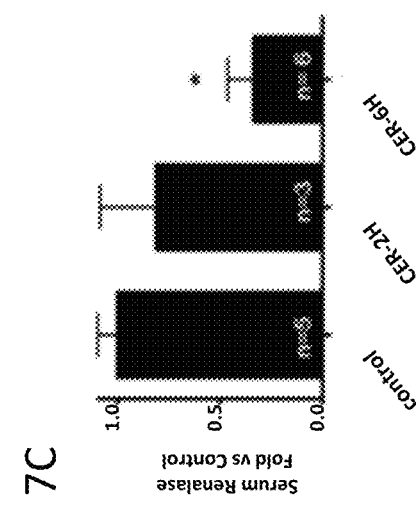
Fig. 7C
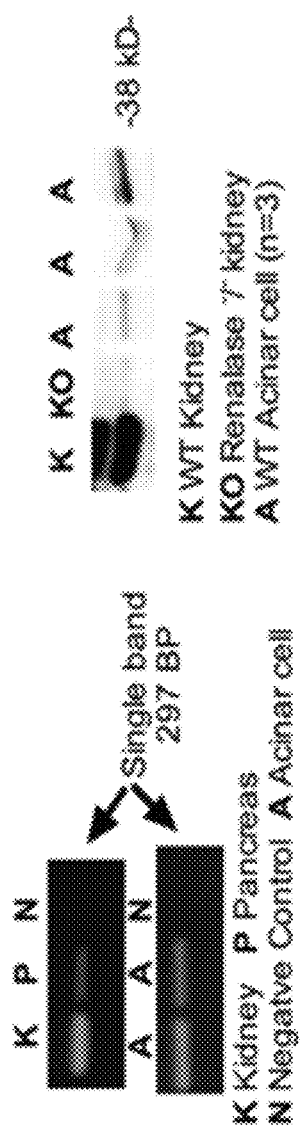
Fig. 7B
Fig. 7A

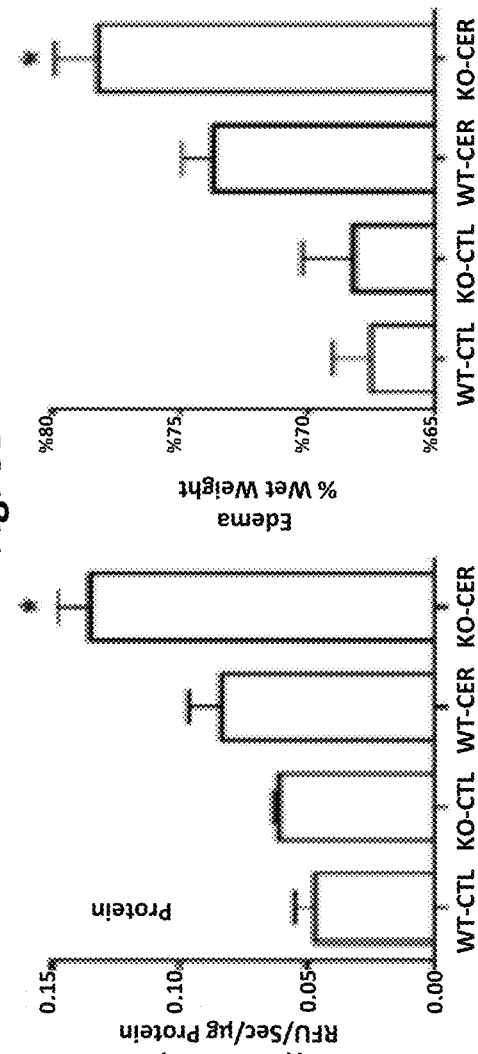
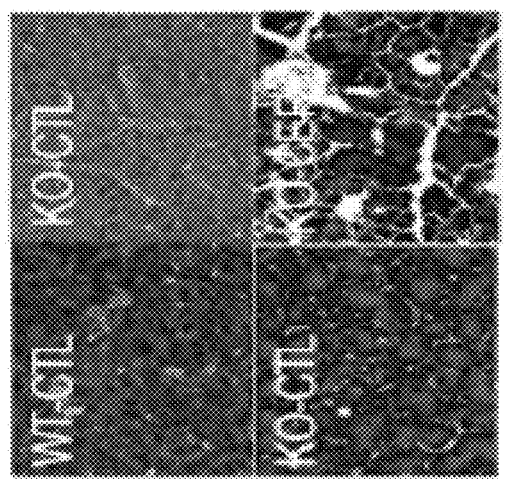
Fig. 8A  Fig. 8B  Fig. 8C

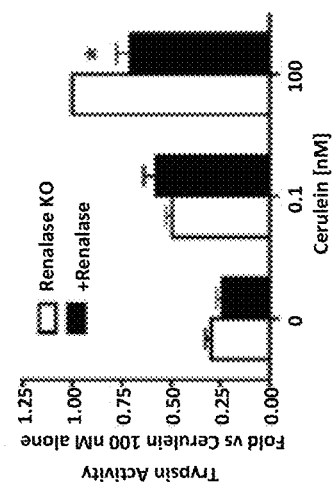
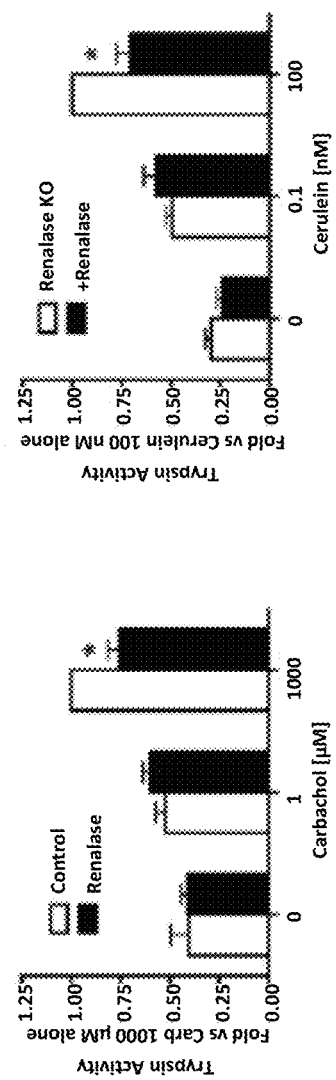
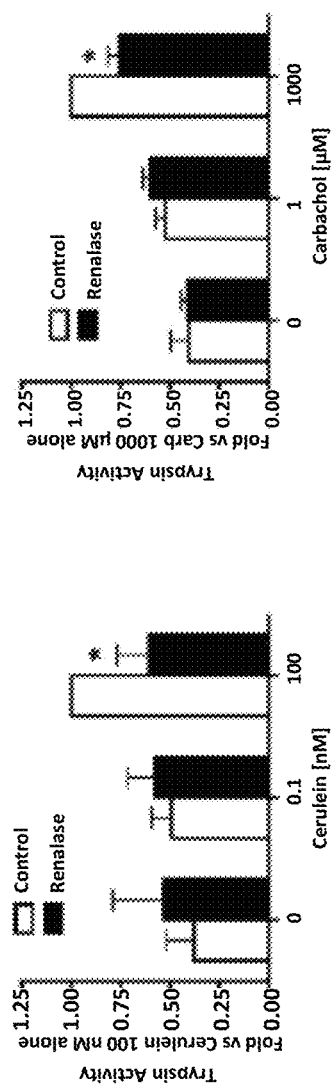
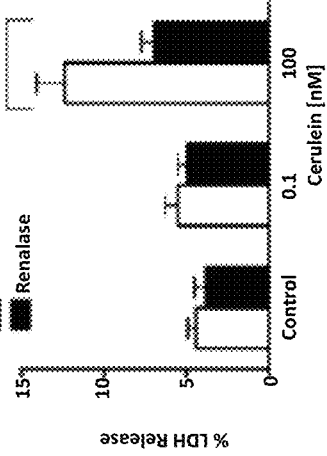
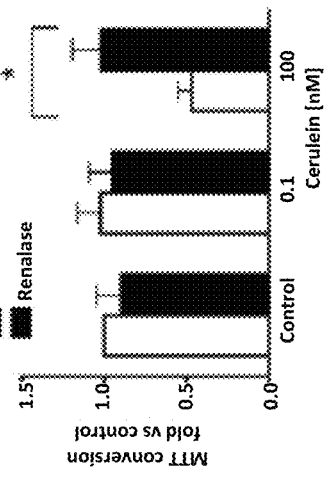

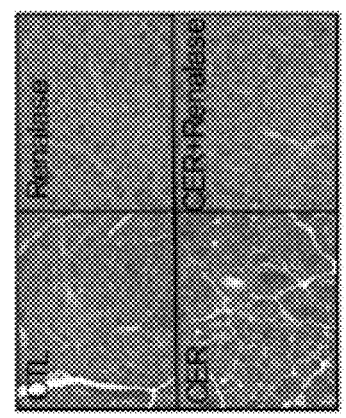
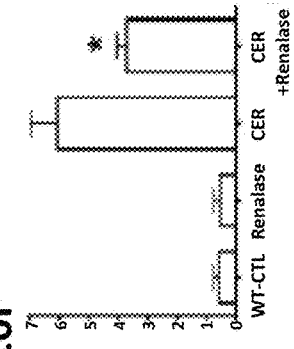
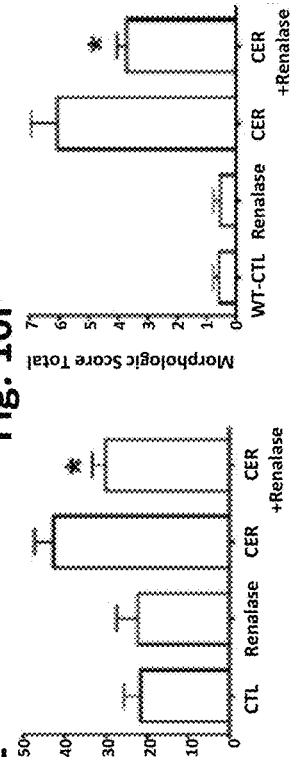
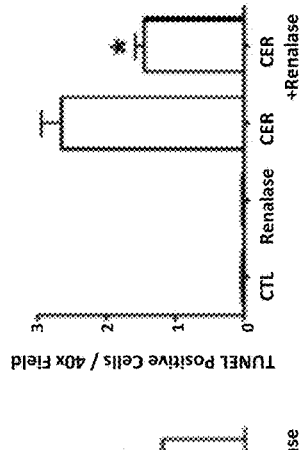
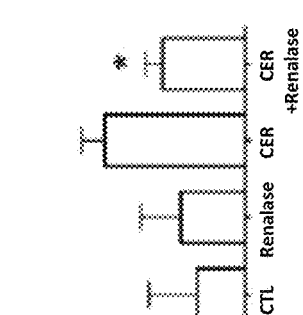
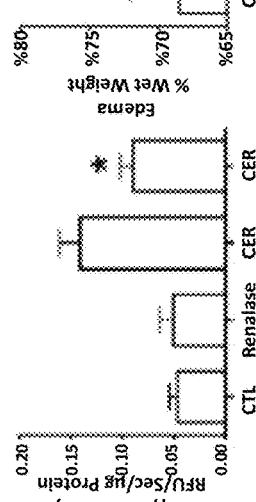
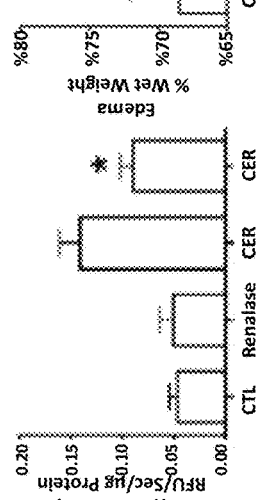

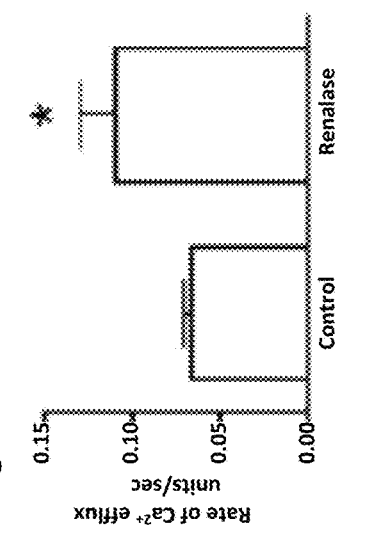
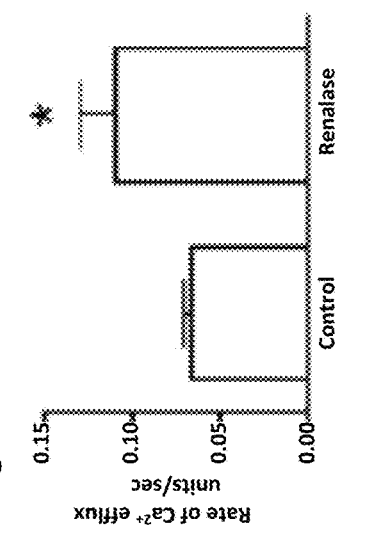
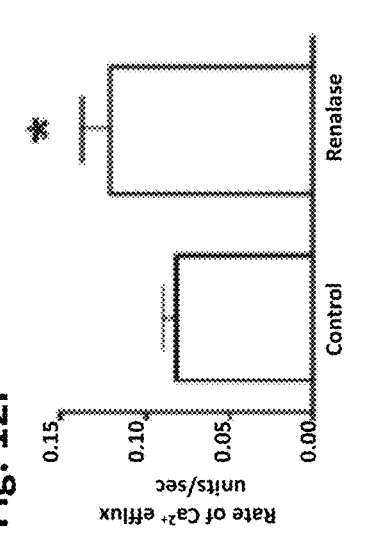
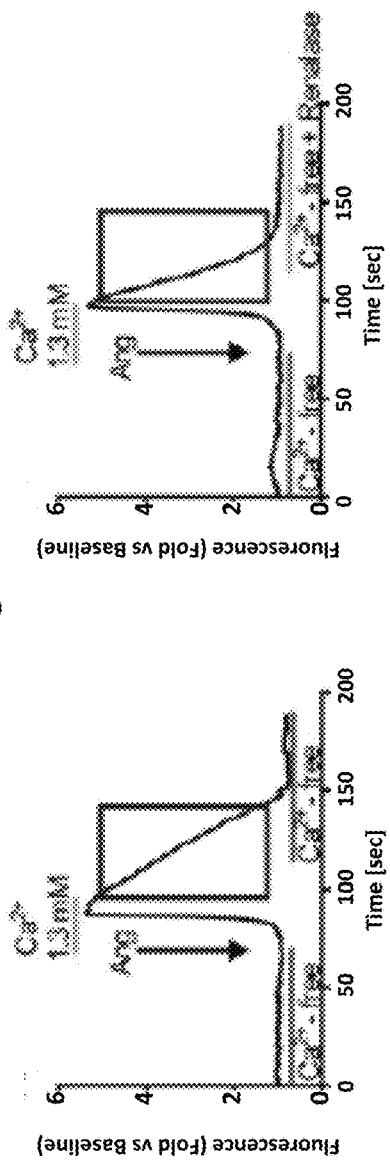
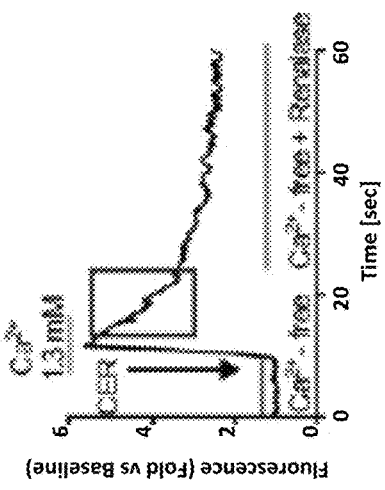
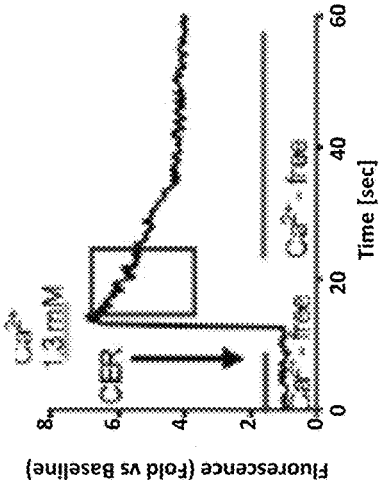

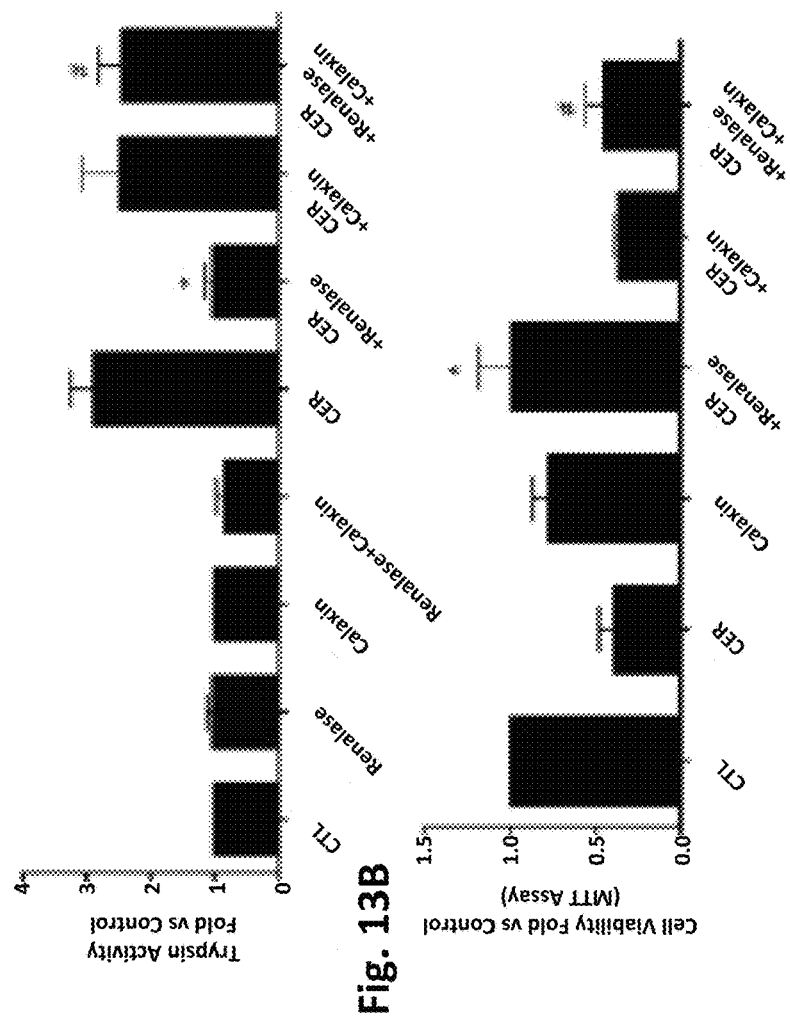

SEQUENCE LISTING

<160> NUMBER OF SEQ ID NOS: 9

<210> SEQ ID NO 1
<211> LENGTH: 20
<212> TYPE: PRT
<213> ORGANISM: Homo sapiens

<400> SEQUENCE: 1

Leu Leu Arg Arg Gln Thr Ser Gly Pro Leu Tyr Leu Ala Val Trp Asp
1               5                   10                  15

Lys Ala Glu Asp
            20

<210> SEQ ID NO 2
<211> LENGTH: 20
<212> TYPE: PRT
<213> ORGANISM: Homo sapiens

<400> SEQUENCE: 2

```
Phe Arg His Arg Val Thr Gln Ile Asn Leu Arg Asp Asp Lys Trp Glu
1               5                   10                  15

Val Ser Lys Gln
            20

<210> SEQ ID NO 3
<211> LENGTH: 11
<212> TYPE: PRT
<213> ORGANISM: Homo sapiens

<400> SEQUENCE: 3

Cys Val Ser Ile Asp Asn Lys Lys Arg Asn Ile
1               5                   10

<210> SEQ ID NO 4
<211> LENGTH: 20
<212> TYPE: PRT
<213> ORGANISM: Homo sapiens

<400> SEQUENCE: 4

Cys Ile Arg Phe Val Ser Ile Asp Asn Lys Lys Arg Asn Ile Glu Ser
1               5                   10                  15

Ser Glu Ile Gly
            20

<210> SEQ ID NO 5
<211> LENGTH: 26
<212> TYPE: PRT
<213> ORGANISM: Homo sapiens

<400> SEQUENCE: 5

His His His His His His Cys Ile Arg Phe Val Ser Ile Asp Asn Lys
1               5                   10                  15

Lys Arg Asn Ile Glu Ser Ser Glu Ile Gly
            20                  25

<210> SEQ ID NO 6
<211> LENGTH: 19
<212> TYPE: PRT
<213> ORGANISM: Homo sapiens

<400> SEQUENCE: 6

Ile Arg Phe Val Ser Ile Asp Asn Ala Ala Ala Asn Ile Glu Ser Ser
1               5                   10                  15

Glu Ile Gly

<210> SEQ ID NO 7
<211> LENGTH: 19
<212> TYPE: PRT
<213> ORGANISM: Homo sapiens

<400> SEQUENCE: 7

Cys Ser Lys Arg Ile Phe Lys Val Ile Ser Ser Ile Glu Asp Asn Asn
1               5                   10                  15

Glu Arg Gly

<210> SEQ ID NO 8
<211> LENGTH: 342
<212> TYPE: PRT
<213> ORGANISM: Homo sapiens

<400> SEQUENCE: 8
```

```
Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Glu Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
        275                 280                 285

Arg His Ser Gln Val Thr Asn Ala Ala Ala Asn Cys Pro Gly Gln Met
    290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
                325                 330                 335

Ala Leu Lys Asn Tyr Ile
            340

<210> SEQ ID NO 9
<211> LENGTH: 315
<212> TYPE: PRT
<213> ORGANISM: Homo sapiens

<400> SEQUENCE: 9

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
```

```
                    20                  25                  30
Trp Asp Lys Ala Glu Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
        50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
                100                 105                 110

Ser Ile Ile Lys His Tyr Leu Lys Glu Ser Gly Ala Glu Val Tyr Phe
                115                 120                 125

Arg His Arg Val Thr Gln Ile Asn Leu Arg Asp Asp Lys Trp Glu Val
                130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Gln Leu Glu Ala Val Ser Tyr Ser Ser
                180                 185                 190

Arg Tyr Ala Leu Gly Leu Phe Tyr Glu Ala Gly Thr Lys Ile Asp Val
                195                 200                 205

Pro Trp Ala Gly Gln Tyr Ile Thr Ser Asn Pro Cys Ile Arg Phe Val
        210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
                260                 265                 270

Ile Leu Pro Gly Leu Pro Gln Pro Ile Ala Thr Lys Cys Gln Lys Trp
        275                 280                 285

Arg His Ser Gln Val Pro Ser Ala Gly Val Ile Leu Gly Cys Ala Lys
        290                 295                 300

Ser Pro Trp Met Met Ala Ile Gly Phe Pro Ile
305                 310                 315
```

COMPOSITIONS AND METHODS FOR TREATING AND PREVENTING PANCREATITIS, RENAL INJURY AND CANCER

CROSS-REFERENCE TO RELATED APPLICATIONS

This application is a continuation of U.S. patent application Ser. No. 15/311,689, filed Nov. 16, 2016, which is a U.S. national phase application filed under 35 U.S.C. § 371 claiming benefit to International Patent Application No. PCT/US15/030980, filed May 15, 2015, which is entitled to priority under 35 U.S.C. § 119(e) to U.S. Provisional Patent Application No. 61/994,279, filed May 16, 2014, each of which application is hereby incorporated herein by reference in its entirety.

STATEMENT REGARDING FEDERALLY SPONSORED RESEARCH OR DEVELOPMENT

This invention was made with government support under grants RC1DK086465, RC1DK086402 and R01DK081037, awarded by the National Institutes of Health. The government has certain rights in the invention.

BACKGROUND OF THE INVENTION

Renalase (also designated RNLS and gene C10orf59) is a novel secretory flavoprotein oxidase (Farzaneh-Far et al., 2010, PLoS One 5:e13496; Desir et al., 2012, J. Am. Heart Assoc. 1:e002634; Desir et al., 2012, 6:417-426; J. Am. Soc. Hypertension; Xu et al., 2005, J. Clin. Invest. 115:1275-1280; Li et al., 2008, Circulation 117:1277-1282). Single nucleotide polymorphisms present in the gene are associated with hypertension, cardiac disease and diabetes (Farzaneh-Far et al., 2010, PLoS One 5:e13496; Barrett et al., 2009, Nat. Genet. 41:703-707; Buraczynska et al., 2011, Neuromolecular Med. 13:321-327; Malyszko et al., 2012, Ren. Fail. 34:727-731; Zhao et al., 2007, J. Mol. Med. (Berl). 85:877-885). Renalase's crystal structure has been solved (Milani et al., 2011, J. Mol. Biol. 411:463-473), and the protein binds epinephrine (Xu et al., 2005, J. Clin. Invest. 115:1275-1280) and functions as an oxidase/anomerase, using molecular oxygen to convert α-NAD(P)H to β-NAD+, with hydrogen peroxide as reaction byproduct (Beaupre et al., 2013, J. Am. Chem. Soc. 135:13980-13987).

The administration of renalase in wild type (WT) mice lowers plasma catecholamines and systemic blood pressure. Renalase deletion in mice (renalase KO) raises catecholamine levels and blood pressure (Wu et al., 2011, Kidney Int. 79:853-860). Gene deletion also aggravates acute ischemic kidney (AKI) (Lee et al., 2013, J. Am. Soc. Nephrol. 24:445-455), and cardiac injury (Wu et al., 2011, Kidney Int. 79:853-860). Recombinant renalase prevents ischemic injury in wild type mice (Lee et al., 2013, J. Am. Soc. Nephrol. 24:445-455). Two single nucleotide polymorphisms (SNPs) in the renalase gene (rs2576178 GG genotype and rs2296545 CC) are associated with essential hypertension (Zhao et al., 2007, J. Mol. Med. (Berl.) 85:877-885). Moreover, rs2296545 CC results in a conservative amino acid change (glutamic to aspartic acid at amino acid 37), and is associated with cardiac hypertrophy, ventricular dysfunction, poor exercise capacity, and inducible ischemia in persons with stable coronary artery disease (Farzaneh-Far et al., 2010, PLoS One 5:e13496). A significant reduction in cardiac renalase levels was observed in a rat model of chronic kidney disease (5/6 Nx) (Li et al., 2008, Circulation 117:1277-1282). Administration of recombinant renalase decreases blood pressure in rodents (Xu et al., 2005, J. Clin. Invest 115:1275-1280; Milani et al., 2011, J. Mol. Biol. 411:463-473), and protects mice against ischemic AKI (Lee et al., 2013, J. Am. Soc. Nephrol. 24:445-455). Renalase also acts as an oxidase/anomerase to convert α-NAD(P)H to β-NAD+, with hydrogen peroxide as reaction byproduct. Independent of its intrinsic enzymatic activities, extracellular renalase activates MAPK signaling and prevents acute kidney injury (AKI) in wild type (WT) mice (Wang et al., 2014, J. Am. Soc. Nephrol. DOI:10.1681/asn.2013060665).

Renalase has cytoprotective effects that are initiated in renal injury via a pattern of MAPK signaling, and that this signaling is mediated by an interaction of renalase with a plasma membrane Ca ATPase. Renal injury can lead to chronic kidney disease (CKD), which is associated with increased morbidity and mortality, is largely due to cardiovascular complications. Approximately 30% of veterans suffer from chronic kidney disease (CKD), which is associated with increased morbidity and mortality, largely due to cardiovascular complications. Acute kidney injury (AKI) is a clinical condition commonly associated with sepsis, surgery, and certain drugs, and which affects up to 20% of hospitalized veterans. Epidemiologic data indicate that severity of AKI is associated with in-hospital and long-term mortality. Increased sympathetic tone has been shown to be pathogenic in CKD and AKI.

Although renalase's crystal structure has been solved, its mechanism of action remains uncertain. It has been recently reported that renalase promotes cell and organ survival through a receptor-mediated process that is independent of its intrinsic enzymatic activities (Wang L, Velazquez H, Moeckel G et al. Renalase Prevents AKI Independent of Amine Oxidase Activity. J Am Soc Nephrol 2014). Renalase was also discovered to activate B-cell lymphoma 2 (Bcl-2), and inhibition of c-Jun N-terminal kinase (JNK).

Acute pancreatitis is a potentially life-threatening disease that affects more than 250,000 people each year in the United States, making it the leading cause of hospitalization for gastrointestinal disorders (Wu and Banks, 2013, Gastroenterology 144, 1272-1281; Whitcomb, 2006, N Engl J Med 354, 2142-2150). Because the pathogenesis of acute pancreatitis is incompletely understood, the mainstay of treatment continues to be supportive care. As a result, there remains a 10-30% mortality rate among patients with severe acute pancreatitis (Petrov et al., 2010, Gastroenterology 139, 813-820; McKay and Imrie, 2004, The British journal of surgery 91, 1243-1244).

This acute inflammatory disease of the pancreas is believed to most often begin by injury to the pancreatic acinar cell. Though abnormalities in acinar cell signaling mediated by protein kinase C isoforms, AMPK, and NFκB have been found early in disease, most studies suggest that abnormalities in cytosolic $Ca^{2+}$ signaling may be the most important for disease initiation. A series of sequential events involving vascular damage with enhanced permeability, inflammation, and reduced blood flow then follow and culminate in pancreatic cell death. In individuals with severe disease, there is multi-organ damage that typically involves the lungs and kidneys. That pancreatitis represents a series of distinct temporal events means that interventions aimed at preventing disease or decreasing its severity should be appropriate disease-stage specific mechanisms to be effective.

Acute pancreatitis has a highly variable clinical course, with possible outcomes ranging from complete recovery to death. Therefore, predicting which patients will develop severe disease is essential to appropriately triage patients (Mounzer et al., 2012, Gastroenterology 142, 1476-1482). At initial patient presentation, measures of kidney function, including blood urea nitrogen (BUN) and creatinine, are among the most reliable predictors of a severe disease course and mortality (Wu et al., 2011, Archives of internal medicine 171, 669-676; Muddana et al., 2009, The American journal of gastroenterology 104, 164-170). Thus, AKI in the setting of acute pancreatitis is associated with a 10-fold increase in mortality (Kes et al., 1996, Ren Fail 18, 621-628; Tran et al., 1993, Nephrol Dial Transplant 8, 1079-1084).

The presence of pre-existing CKD and end stage renal disease (ESRD) also predispose to acute pancreatitis and worsen its severity. Patients with CKD and ESRD are up to 50-times more likely to develop acute pancreatitis than matched controls (Lankisch et al., 2008, Nephrol Dial Transplant 23, 1401-1405; Rutsky et al., 1986, Archives of internal medicine 146, 1741-1745; Quraishi et al., 2005, The American journal of gastroenterology 100, 2288-2293). Additionally, CKD patients with acute pancreatitis have a higher likelihood of serious complications and death (Pitchumoni et al., 1996, The American journal of gastroenterology 91, 2477-2482; Golay and Roychowdhary, 2012, Ren Fail 34, 1338-1340). The etiology of acute pancreatitis in patients with CKD is unknown in the majority of cases, suggesting that CKD might sensitize to the development of acute pancreatitis (Pitchumoni et al., 1996, The American journal of gastroenterology 91, 2477-2482). One study demonstrated that acute renal failure in rats causes a distinct pattern of pancreatic injury (Lerch et al., 1994, Gut 35, 401-407), but whether it sensitizes to the development or severity of experimental pancreatitis is unknown. An understanding of the mechanisms responsible for the sensitizing effects of AKI and CKD on acute pancreatitis could lead to targeted therapies.

There is thus a need in the art for compositions and methods for the treatment and prevention of renal injury, such as AKI and CKD, and pancreatitis. The present invention addresses this unmet need in the art.

SUMMARY OF THE INVENTION

In one embodiment, the invention is a method of treating or preventing a renal disease or disorder in a subject in need thereof, by administering to the subject a therapeutically effective amount of a composition comprising at least one PMCA4b activator. In various embodiments, the PMCA4b activator is a chemical compound, a protein, a peptide, a peptidomemetic, an antibody, a small molecule chemical compound, or a combination thereof. In one embodiment, the PMCA4b activator is a renalase polypeptide, or a fragment or conjugate or analogue or homolog thereof. In one embodiment, the renalase polypeptide comprises the amino acid sequence of SEQ ID NO: 8, or a fragment or conjugate or analogue or homolog thereof. In another embodiment, the renalase polypeptide comprises the amino acid sequence of SEQ ID NO: 9, or a fragment or conjugate or analogue or homolog thereof. In another embodiment, the PMCA4b activator is a renalase polypeptide fragment. In one embodiment, the renalase polypeptide fragment comprises the amino acid sequence of SEQ ID NO: 3, or a fragment or conjugate or analogue or homolog thereof. In another embodiment, the renalase polypeptide fragment comprises the amino acid sequence of SEQ ID NO: 4, or a fragment or conjugate or analogue or homolog thereof. In one embodiment, the renalase polypeptide fragment comprises the amino acid sequence of SEQ ID NO: 5, or a fragment or conjugate or analogue or homolog thereof. In some embodiments, the at least one PMCA4b activator is administered one time. In some embodiments, the at least one PMCA4b activator is administered repeatedly. In some embodiments, the at least one PMCA4b activator is administered locally, regionally or systemically. In various embodiments, the PMCA4b activator is an activator of PMCA4b expression, an activator of PMCA4b activity, or a combination thereof. In various embodiments, the renal disease or disorder that is treated or prevented is selected from the group consisting of acute kidney injury (AKI), chronic kidney disease (CKD), renal ischemic injury, renal reperfusion injury, renal ischemic-reperfusion injury, toxic renal injury, renal tubular necrosis, renal tubular inflammation, renal tubular apoptosis, hypertension, and any combination thereof. In one embodiment, the subject is human.

In another embodiment, the invention is a method of treating or preventing cancer in a subject in need thereof, by administering to the subject a therapeutically effective amount of a composition comprising at least one PMCA4b inhibitor. In various embodiments, the PMCA4b inhibitor is a chemical compound, a protein, a peptide, a peptidomemetic, an antibody, a ribozyme, a small molecule chemical compound, an antisense nucleic acid molecule, or any combination thereof. In one embodiment, the PMCA4b inhibitor is caloxin 1b, or analogue or homolog thereof. In another embodiment, the PMCA4b inhibitor is cisplatin, or analogue or homolog thereof. In various embodiments, the cancer that is treated or prevented is selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, or any combination thereof. In one embodiment, the subject is human.

In one embodiment, the invention is a method of treating or preventing a pancreatic disease or disorder in a subject in need thereof, by administering to the subject a therapeutically effective amount of a composition comprising at least one agent, wherein the at least one agent is at least one selected from the group consisting of a renalase polypeptide, a renalase polypeptide fragment, and an activator of renalase, or a fragment or conjugate or analogue or homolog thereof. In one embodiment, the renalase polypeptide is a recombinant renalase polypeptide, or a fragment or conjugate or analogue or homolog thereof. In another embodiment, the renalase polypeptide comprises the amino acid sequence of SEQ ID NO: 8, or a fragment or conjugate or analogue or homolog thereof. In one embodiment, the renalase polypeptide comprises the amino acid sequence of SEQ ID NO: 9, or a fragment or conjugate or analogue or homolog thereof. In another embodiment, the renalase polypeptide fragment comprises the amino acid sequence of SEQ ID NO: 3, or a fragment or conjugate or analogue or homolog thereof. In one embodiment, the renalase polypeptide fragment comprises the amino acid sequence of SEQ ID NO: 4, or a fragment or conjugate or analogue or homolog thereof. In another embodiment, the renalase polypeptide fragment comprises the amino acid sequence of SEQ ID NO: 5, or a fragment or conjugate or analogue or homolog thereof. In some embodiments, the at least one agent is administered one time. In some embodiments, the at least one agent is administered repeatedly. In various embodiments, the at least one agent is administered locally, regionally or systemically. In one embodiment, the activator of renalase is an activator of renalase expression, an activator of renalase activity, or a combination thereof. In various embodiments, the activator of renalase is a chemical compound, a protein, a peptide, a peptidomemetic, a small molecule chemical compound, or a combination thereof. In various embodiments, the pancreatic disease or disorder is at least one selected from the group consisting of acute pancreatitis and chronic pancreatitis.

In one embodiment, the invention is a method of diagnosing a pancreatic disease or disorder in a subject in need thereof, including the steps of determining the level of renalase in a biological sample of the subject, comparing the level of renalase in the biological sample of the subject with a comparator control, and diagnosing the subject with a pancreatic disease or disorder when the level of renalase in the biological sample of subject is reduced when compared with the level of renalase of the comparator control. In one embodiment, the method also includes the step of administering a treatment to the subject that was diagnosed as having a pancreatic disease or disorder. In some embodiments, the level of renalase in the biological sample is determined by measuring the level of renalase mRNA in the biological sample. In some embodiments, the level of renalase in the biological sample is determined by measuring the level of renalase polypeptide in the biological sample. In some embodiments, the level of renalase in the biological sample is determined by measuring an enzymatic activity of renalase polypeptide in the biological sample. In various embodiments, the comparator control is at least one selected from the group consisting of: a positive control, a negative control, a historical control, a historical norm, or the level of a reference molecule in the biological sample. In various embodiments, the pancreatic disease or disorder acute pancreatitis or chronic pancreatitis. In one embodiment, the subject is human.

In another embodiment, the invention is a method of identifying a test compound as a modulator of the activity of a renalase receptor, including the steps of determining the level of activity of a renalase receptor in the presence of a test compound, determining the level of activity of a renalase receptor in the absence of a test compound, comparing the level of activity of a renalase receptor in the presence of the test compound with the level of activity of a renalase receptor in the absence of the test compound, identifying the test compound as a modulator of the activity of a renalase receptor when the level of activity of a renalase receptor in the presence of the test compound is different than the level of activity of a renalase receptor in the absence of the test compound. In some embodiments, when the level of activity of a renalase receptor is increased in the presence of the test compound, the test compound is identified as an activator. In some embodiments, when the level of activity of a renalase receptor is reduced in the presence of the test compound, the test compound is identified as an inhibitor. In one embodiment, the level of activity of a renalase receptor is determined by measuring the level of mitogen-activated protein kinase (MAPK) signaling. In one embodiment, the level of activity of a renalase receptor is determined by measuring ATPase activity. In one embodiment, the renalase receptor is PMCA4b. In various embodiments, the test compound is a chemical compound, a protein, a peptide, a peptidomemetic, an antibody, a nucleic acid, an antisense nucleic acid, an siRNA, a miRNA, a shRNA, a ribozyme, an allosteric modulator, a small molecule chemical compound, or a combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A is an illustration depicting the amino acid sequence of renalase peptides (SEQ ID NOs 1-7): RP-Scr220 (SEQ ID NO: 7): scrambled RP-220. FIG. 1B is a graph depicting the effect of renalase peptides on survival of HK-2 cells exposed to 20 μM cisplatin for 24 hrs; cell survival is depicted as % change in survival compared to that in cisplatin-treated HK-2 cells without renalase peptides; cell survival was measured by the WST-1 method; RP-A220: mutated RP-220, and RP-19 and RP-128: control peptides; peptide concentration (μg/ml) indicated in top line; n=4, *=p<0.05. FIG. 1C is a graph depicting a comparison of protective effect of recombinant renalase; RP-224, RP-220, and RP-H220 on survival of HK-2 cells exposed to 20 μM cisplatin for 24 hrs; cell survival is depicted as % change in survival compared to that in cisplatin-treated HK-2 cells without renalase peptides; n=4, *=p<0.05. FIG. 1D is a graph depicting a dose response curve for RP-220 and RP-H220; HK-2 cells were exposed to 20 μM cisplatin for 24 hrs; cell survival is depicted as % change in survival compared to that in cisplatin-treated HK-2 cells without renalase peptides; n=4, *=p<0.05

FIG. 2A is an image of a gel depicting MAPK phosphorylation with cisplatin alone (CP) and with CP and RP-220; representative study: p-p38: phosphorylated p38 MAPK; p-ERK: phosphorylated ERK. FIG. 2B is a graph depicting quantification of ERK activation. Signals were normalized to glyceraldehyde 3-phosphate dehydrogenase (GAPDH) loading control; n=3, *=P<0.05. FIG. 2C is a graph depicting quantification of p38 activation, signals normalized to GAPDH loading control; n=3, *=P<0.05.

FIG. 3A is a graph depicting how the inhibition of either p38 (SB203580) or ERK (U0126) did not adversely affect the survival of HK-2 cells measured using the WST-1 method; cell survival is depicted as % change in survival compared to that of untreated HK-2 cells; n=4, *=P<0.05. FIG. 3B is a graph depicting how the inhibition of p38 (10 μM SB203580) abrogated the protective action of RP-220 for HK-2 cells exposed to 20 μM cisplatin (Cis) for 24 hrs; n=4, *=P<0.05.

FIGS. 4A-4D, depict the identification of plasma membrane calcium ATPase isoform PMCA4b as a renalase binding protein. FIG. 4A is an image of a gel depicting HK-2 cells incubated with either labeled RP-Scr220 or RP-220, biotin-labeled proteins purified using streptavidin column, separated by SDS-PAGE and visualized by western blot using streptavidin-HRP; *=regions evaluated by mass spectrometry in samples labeled with either RP-Scr220 or RP-220; #=RP-220 band containing the plasma membrane calcium ATPase isoform PMCA4b. FIG. 4B is an image of a gel depicting the endogenous expression of PMCA4b in HK-2 cells, western immunoblot using isoform specific monoclonal; CCL-119: human leukemic cell line; thyroid tumor=human thyroid tumor cell line (ATCC, CRL-1803)

10 µg protein loaded in each lane. FIG. 4C is an image of co-immunolocalization of PMCA4b and renalase in HK-2 cells. Images were acquired using a Zeiss laser scanning confocal microscope; scale bar=9 µm; arrow=plasma membrane; FIG. 4D is an image of gel depicting co-immunoprecipitation of PMCA4b and renalase from HK-2 cell lysates; renalase-Ab-beads=renalase antibody coated beads; PMCA4b-Ab-beads=PMCA4b antibody coated beads.

FIG. 1A is a series of panels depicting how PMCA4b inhibition abrogates RP-220 mediated ERK and p38 signaling in HK-2 cells; caloxin1b=peptide inhibitor of PMCA4; left panel: RP-220 mediated ERK and p38 activation, phospho=phosphorylated, representative blot; middle panel: inhibition of RP-220 mediated ERK and p38 activation by caloxin1b (100 µM); right panel: quantification of phosphorylated p38 (P-p38) and phosphorylated ERK (p-ERK); signals were normalized to glyceraldehyde 3-phosphate dehydrogenase (GAPDH) loading control; n=3, *=P<0.05. FIG. 5B is a series of panels depicting how siRNA mediated inhibition of PMCA4b expression downregulates RP-220 mediated MAPK signaling; left panel: RP-220 mediated ERK and p38 activation in HK-2 cells transfected with non-targeting siRNA, p=phosphorylated, representative immunoblot; middle panel: inhibition of RP-220 mediated ERK and p38 activation in HK-2 cells transfected with PMCA4b siRNA, representative blot; right panel: quantification of phosphorylated ERK (p-ERK), signals normalized to glyceraldehyde 3-phosphate dehydrogenase (GAPDH) loading control; n=3, *=P<0.05. FIG. 5 is a series of panels depicting the lack of effect of siRNA mediated inhibition of PMCA4b expression on epidermal growth factor (EGF)-mediated MAPK signaling; left panel: EGF (100 ng/ml) mediated ERK, p38 activation and c-Jun N-Terminal Kinase (JNK) in HK-2 cells transfected with non-targeting siRNA, p=phosphorylated, representative blot; right panel: EGF-mediated ERK, p38 and JNK activation in HK-2 cells unaffected by transfection with PMCA4b siRNA and downregulation of PMCA4b expression; representative blot (n=3). FIG. 5D is a graph depicting how the inhibition of PMCA4b expression abrogates protective effect of renalase peptides for HK-2 cells exposed to cisplatin: HK-2 cells exposed to 20 cisplatin for 24 hrs; cell survival is depicted as % change in survival compared to that in cisplatin-treated HK-2 cells without renalase peptides; cell survival was measured by the WST-1 method, peptide concentration 15 µg/ml, indicated in top line; n=4, *=p<0.05. FIG. 5E is an image of a gel depicting endogenous expression of PMCA4b in WT and renalase KO mice; western immunoblot using an anti-renalase monoclonal antibody; 10 µg protein loaded in each lane.

(FIG. 6A) HK-2 cells incubated with either labeled RP-Scr220 or RP-220, biotin-labeled proteins purified using streptavidin column, separated by SDS-PAGE and visualized by western blot using streptavidin-HRP; *=regions evaluated by mass spectrometry in samples labeled with either RP-Scr220 or RP-220; # RP-220 band containing the plasma membrane calcium ATPase isoform PMCA4b. (FIG. 6B) Co-immunolocalization of PMCA4b and renalase in HK-2 cells, images acquired using a Zeiss laser scanning confocal microscope; arrow points to plasma membrane. (FIG. 6C) Co-immunoprecipitation of PMCA4b and renalase from HK-2 cell lysates; renalase-Ab-beads=renalase antibody coated beads; PMCA4b-Ab-beads=PMCA4b antibody coated beads. (FIG. 6D) Inhibition of PMCA4b expression abrogates protective effect of renalase peptides for HK-2 cells exposed to cisplatin: HK-2 cells exposed to 20 µM cisplatin for 24 hrs; cell survival is depicted as % change in survival compared to that in cisplatin-treated HK-2 cells without renalase peptides; cell survival measured by the WST-1 method, peptide concentration 15 µg/ml, indicated in top line; n=4, *=p<0.05.

FIGS. 7A-7C, depict the results of experiments showing that renalase is present in mouse acinar cells and its levels are reduced in the serum after inducing acute experimental pancreatitis. FIGS. 7A and 7B show that renalase is expressed in the pancreatic acinar cell, but at lower levels than the kidney. Since renalase is present in the serum (FIG. 7C), renalase could affect the acinar cells through autocrine/paracrine pathways and also as a hormone. Serum renalase levels decrease in a time-dependent manner in mice after initiating cerulein-induced pancreatitis, falling by about 70% after 7 hrs of cerulein pancreatitis (FIG. 7C). This finding has several important implications: i) the protective effects of serum renalase can be lost during the onset of acute pancreatitis and ii) renalase is useful as a disease biomarker.

FIGS. 8A-8C, depict the results of experiments showing renalase deficiency worsens cerulean pancreatitis in vivo. Wild-type (WT) mice or renalase deficient knock-out (KO) mice were treated with 6 hourly IP injections of cerulein (CER, 40 mcg/kg). (FIG. 8A) Pancreatic trypsin activation measured with fluorogenic substrate, normalized to total protein. (FIG. 8B) Edema measured as % wet weight. Pancreas H&E sections (FIG. 8C) showed more edema and vacuolization compared with WT. *p<0.05 vs. WT-CER, +/−SEM, n=5.

FIGS. 9A-9E, depict the results of experiments that show recombinant exogenous renalase reduce zymogen activation and injury in vitro in mice. (FIG. 9A) Isolated WT mouse acini were pretreated for 30 minutes with recombinant renalase (25 µg/mL; 0.1 µM) and then treated with either (FIG. 9A, 9D, 9E) physiologic (0.1 nM) and supraphysiologic (100 nM) cerulein or (FIG. 9B) physiologic (1 µM) or supraphysiologic (1000 µM) carbachol for 30 minutes. Trypsin activity (FIGS. 9A-9C), MTT accumulation (FIG. 9D), and LDH release (FIG. 9E) were assayed using a fluorogenic substrate. For FIG. 9C, isolated acini from renalase $^{-/-}$ mice were treated pretreated with recombinant renalase (25 µg/mL) and then treated with cerulein (0.1 nM or 100 nM) for 30 minutes. *p<0.05 vs. supraphysiologic cerulein or carbachol, # p<0.05 vs. WT, n=3, +/−SEM.

FIGS. 10A-10G, depict the results of experiments showing that pretreatment with renalase peptide (RP-220) ameliorates cerulein-induced pancreatitis in vivo. WT mice were treated with 6 hourly IP injections of cerulein (CER, 40 mcg/kg). IP renalase peptide, RP-220 (renalase, 1.3 mg/kg) was given 1 hour before first cerulein injection. (FIG. 10A) Pancreatic trypsin activation measured with fluorogenic substrate, normalized to total protein. (FIG. 10B) Edema measured as % wet weight. (FIG. 10C) Apoptosis evaluated by TUNEL positive cells. (FIG. 10D) Neutrophils (Ly-6B) and (FIG. 10E) macrophages (F4/80) were quantified. Pancreas H&E sections (FIG. 10G) were evaluated for edema, pyknotic nucei, and vacuoles to derive morphological score (FIG. 10F). *p<0.05 vs. WT-CER, +/−SEM, n=5.

FIGS. 12A-12F, depict the results of experiments showing renalase increases $Ca^{2+}$ efflux through PCMA. Changes in whole cell cytosolic $Ca^{2+}$ were recorded with the $Ca^{2+}$ dye Fluo-4 (HK2 cells) or Fluo-5 (acinar cell) by time lapse confocal microscopy. FIGS. 12A, 12B, 12D, and 12E are representative plots of fluorescence over time in HK2 cells (FIGS. 12A and 12B) or mouse acinar cells (FIGS. 12D and 12E). Cells were pretreated with 30 µM cyclopiazonic acid and perfused with $Ca^{2+}$-free medium. Cells were briefly stimulated with 10 nM angiotensin IV (Ang in HK2 cells) or 100 nM cerulein (Cer in acinar cells) in the presence of 1.3 mM $Ca^{2+}$. Next, cells were again perfused with $Ca^{2+}$-free media in the absence or presence of recombinant renalase, and $Ca^{2+}$ efflux was observed (box). All buffers in HK2 cells were also $Na^+$-free. For FIGS. 12C and 12F, the rate of $Ca^{2+}$ efflux was quantified from 30 cells/treatment group. *$p<0.05$ vs. no renalase. Mean+/−SEM.

FIGS. 13A-13C, depict the results of experiments showing caloxin blocks the protective effects of renalase. Isolated WT mouse acini were pretreated for 30 minutes with caloxin 1b (100 µM) and/or recombinant renalase (25 µg/mL) and then treated with supraphysiologic (100 nM) cerulein (CER) and assayed for trypsin activity (FIG. 13A) or MTT conversion (FIG. 13B). *$p<0.05$ vs. CER, # $p<0.05$ vs. CER+ renalase. WT, n=3, +/−SEM. H&E sections (FIG. 13C) show that caloxin reverses the protective effects of renalase on edema and vacuole formation (arrows).

DETAILED DESCRIPTION

Figure 1A:
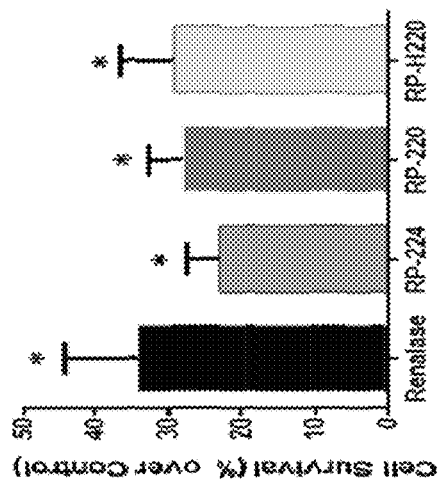
FIGS. 1A-1D, depict how renalase peptides exhibit protective effects.

The present invention relates to the discovery that modulators of renalase receptor PMCA4b are useful the treatment or prevention of various diseases or disorders. In one embodiment, the PMCA4b is a PMCA4b activator. Thus, the present invention relates to compositions comprising a PMCA4b activator and methods for treating and preventing renal and pancreatic diseases or disorders. In some embodiments, the renal disease or disorder treated or prevented using the compositions and methods of the invention is acute kidney injury (AKI) or chronic kidney disease (CKD). In some embodiments, the pancreatic disease or disorder treated or prevented using the compositions and methods of the invention is acute pancreatitis or chronic pancreatitis. In another embodiment, the PMCA4b is a PMCA4b inhibitor. Therefore, the present invention also relates to compositions comprising a PMCA4b inhibitor and methods for treating and preventing cancer.

The present invention also relates to the discovery that renalase, and fragments thereof, are useful for the treatment or prevention of diseases or disorders, such as pancreatitis. Thus, the invention relates to compositions comprising renalase, or fragments thereof, and methods for treating and preventing diseases and disorders, including pancreatic disease or disorders.

The compositions and methods of the invention comprise recombinant renalase, or fragments thereof. In one embodiment, the renalase of the invention is a polypeptide comprising the amino acid sequence of SEQ ID NO: 8. In another embodiment, the renalase of the invention is a polypeptide comprising the amino acid sequence of SEQ ID NO: 9. In some embodiments, the renalase of the invention is a renalase fragment comprising at least a portion of the amino acid sequence of SEQ ID NO: 8 or SEQ ID NO: 9. In some embodiments, the renalase fragment is a peptide that retains its AKI protective activity, but does not exhibit detectable NADH oxidase activity. In some embodiments, the renalase fragment is a peptide that retains its protective activity, but does not exhibit detectable amine oxidase activity. In a particular embodiment, the renalase fragment is a peptide comprising the amino acid sequence of SEQ ID NO: 3. In another particular embodiment, the renalase fragment is a peptide comprising the amino acid sequence of SEQ ID NO: 4. In another particular embodiment, the renalase fragment is a peptide comprising the amino acid sequence of SEQ ID NO: 5.

In one embodiment, the invention is a method of diagnosing a pancreatic disease or disorder, such as pancreatitis, of a subject by assessing the level of renalase in a biological sample of the subject. In one embodiment, a change (i.e., increase or decrease) in the level of renalase compared with a comparator is a marker for the diagnosis of a pancreatic disease or disorder, such as pancreatitis, as well as for monitoring the effectiveness of a treatment of a pancreatic disease or disorder.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" or "treat" a disease means reducing the frequency or severity of at least one sign or symptom of a disease or disorder.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

By the term "applicator," as the term is used herein, is meant any device including, but not limited to, a hypodermic syringe, a pipette, an iontophoresis device, a patch, and the like, for administering the compositions of the invention to a subject.

As used herein, the term "marker" or "biomarker" is meant to include a parameter which is useful according to this invention for determining the presence and/or severity of a disease or disorder, such as AKI or pancreatitis.

The level of a marker or biomarker "significantly" differs from the level of the marker or biomarker in a reference sample if the level of the marker in a sample from the patient differs from the level in a sample from the reference subject by an amount greater than the standard error of the assay employed to assess the marker, and preferably at least 10%, and more preferably 25%, 50%, 75%, or 100%.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein, polypeptide or peptide, refers to a subsequence of a larger protein or peptide. A "fragment" of a protein, polypeptide, or peptide can be at least about 5 amino acids in length; for example, at least about 10 amino acids in length; at least about 20 amino acids in length; at least about 50 amino acids in length; at least about 100 amino acids in length; at least about 200 amino acids in length; or at least about 300 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Instructional material," as that term is used herein, includes a publication, a recording, a diagram, or any other medium of expression which can be used to communicate the usefulness of the nucleic acid, peptide, polypeptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject. The term encompasses activating, inhibiting and/or otherwise affecting a native signal or response thereby mediating a beneficial therapeutic response in a subject, preferably, a human.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "polymerase chain reaction" ("PCR") refers to the method of K. B. Mullis (U.S. Pat. Nos. 4,683,195 4,683,202, and 4,965,188, hereby incorporated by reference) for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

To "prevent" a disease or disorder as the term is used herein, means to reduce the severity or frequency of at least one sign or symptom of a disease or disorder being experienced by a subject.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, "substantially purified" refers to being essentially free of other components. For example, a substantially purified polypeptide is a polypeptide which has been separated from other components with which it is normally associated in its naturally occurring state.

As used herein, the terms "therapy" or "therapeutic regimen" refer to those activities taken to prevent, alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more compounds or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease or disorder as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes the unexpected identification of the renalase receptor PMCA4b, a plasma membrane calcium ATPase. As demonstrated herein, PMCA4b co-localizes with renalase in HK-2 cells, while inhibition of PMCA4b enzymatic activity was found to prevent renalase-mediated mitogen-activated protein kinase (MAPK) signaling in these cells. Therefore the interaction between PMCA4b and recombinant renalase or renalase peptide fragments appears to be critical for initiating a pattern of MAPK signaling, which results in the observed cytoprotective effect of renalase and renalase peptides. Thus, the present invention relates to the discovery that the protective effect of renalase against a disease or disorder is mediated by the interaction of renalase or a short renalase peptide with a renalase receptor. While the preferred renalase receptor is PMCA4b, the invention should be construed to encompass any other receptor that binds to renalase, a renalase fragment, or combinations thereof.

In one aspect of the invention, the compositions and methods of the invention comprise a PMCA4b activator. The compositions and methods of the invention include compositions and methods for treating or preventing disorders and diseases where an increased activity or level of PMCA4b is desirable. In various embodiments, the diseases and disorders where an increased activity or level of PMCA4b is desirable which can be treated or prevented with the compositions and methods of the invention include acute kidney injury (AKI), chronic kidney disease (CKD), renal ischemic injury, renal reperfusion injury, renal ischemic-reperfusion injury, toxic renal injury, renal tubular necrosis, renal tubular inflammation, renal tubular apoptosis, hypertension, pancreatitis, and any combination thereof.

In another aspect of the invention, the compositions and methods of the invention comprise a PMCA4b inhibitor. The compositions and methods of the invention include compositions and methods for treating or preventing disorders and diseases where a decreased activity or level of PMCA4b is desirable. In various embodiments, a disease or disorder where a decreased activity or level of PMCA4b is desirable which can be treated or prevented with the compositions and methods of the invention includes cancer. In one embodiment, the cancer is selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

In another embodiment, the invention is a method of identifying a modulator of a renalase receptor, such as PMCA4b.

In some embodiments, the compositions and methods of the invention comprise renalase, or a fragment thereof, for use in the treatment or prevention of a pancreatic disease or disorder, such as pancreatitis. In some embodiments, the renalase of the invention is a polypeptide comprising the amino acid sequence of SEQ ID NO: 8 or SEQ ID NO: 9. In some embodiments, the renalase of the invention is a renalase fragment comprising at least a portion of the amino acid sequence of SEQ ID NO: 8 or SEQ ID NO: 9. In some embodiments, the renalase fragment is a peptide that retains its protective activity, but does not exhibit detectable NADH oxidase activity. In some embodiments, the renalase fragment is a peptide that retains its protective activity, but does not exhibit detectable amine oxidase activity. In a particular embodiment, the renalase fragment is a peptide comprising the amino acid sequence of SEQ ID NO: 3. In another particular embodiment, the renalase fragment is a peptide comprising the amino acid sequence of SEQ ID NO: 4. In another particular embodiment, the renalase fragment is a peptide comprising the amino acid sequence of SEQ ID NO: 5. In another particular embodiment, the renalase fragment is a peptide consisting of the amino acid sequence of SEQ ID NO: 3. In another particular embodiment, the renalase fragment is a peptide consisting of the amino acid sequence of SEQ ID NO: 4. In another particular embodiment, the renalase fragment is a peptide consisting of the amino acid sequence of SEQ ID NO: 5.

The compositions and methods of the invention comprise recombinant renalase, or fragments thereof. The compositions and methods of the invention include compositions and methods for treating or preventing disorders and diseases where an increased activity or level of renalase is desirable. In various embodiments, the disorders and diseases where an increased activity or level of renalase is desirable which can be treated or prevented with the compositions and methods of the invention include acute pancreatitis or chronic pancreatitis.

In another embodiment, the invention is a method of diagnosing a pancreatic disease or disorder of a subject by assessing the level of renalase in a biological sample of the subject. In one embodiment, a change (i.e., increase or decrease) in the level of renalase compared with a comparator is a marker for the diagnosis of a pancreatic disease or disorder, such as pancreatitis, as well as for monitoring the effectiveness of a treatment of a pancreatic disease or disorder, such as pancreatitis.

PMCA4b Activator Compositions and Methods of Treatment and Prevention

In various embodiments, the present invention includes PMCA4b activator compositions and methods of increasing the level or activity of PMCA4b in a subject, a tissue, or an organ in need thereof. In various embodiments, the PMCA4b activator compositions and methods of treatment of the invention increase the amount of PMCA4b polypeptide, the amount of PMCA4b mRNA, the amount of PMCA4b enzymatic activity, the amount of PMCA4b substrate binding activity, or a combination thereof. In one embodiment, the PMCA4b activator composition comprises a PMCA4b activator. In various embodiments, the diseases and disorders wherein activation of PMCA4b may improve therapeutic outcome include, but are not limited to, AKI, chronic kidney disease (CKD), myocardial necrosis, heart failure, congestive heart failure, cardiac ischemic injury, cardiac reperfusion injury, cardiac ischemic-reperfusion injury, toxic cardiac injury, renal ischemic injury, renal reperfusion injury, renal ischemic-reperfusion injury, toxic renal injury, renal tubular necrosis, renal tubular inflammation, renal tubular apoptosis, ischemic brain injury, reperfusion brain injury, ischemic-reperfusion brain injury, toxic brain injury, ischemic liver injury, reperfusion liver injury, ischemic-reperfusion liver injury, toxic liver injury, pancreatitis, acute pancreatitis, chronic pancreatitis, preservation of organs harvested for transplantation, pheochromocytoma, and hypertension. In some embodiments, the compositions and methods of the invention are useful for controlling or maintaining blood pressure. In some embodiments, the compositions and methods of the invention are useful for treating or preventing sympathetic nervous system diseases and disorders, such as, by way of a non-limiting examples, anxiety, post-traumatic stress disorder (PTSD) and attention deficit hyperactivity disorder (ADHD).

In one aspect, the methods of the present invention include a method of treating or preventing a disease or disorder in a subject in need thereof. In one embodiment, the method comprises administering to the subject a therapeutically effective amount of a composition comprising at least one PMCA4b activator. In one embodiment, the disease or disorder is selected from the group consisting of acute kidney injury (AKI), chronic kidney disease (CKD), renal ischemic injury, renal reperfusion injury, renal ischemic-reperfusion injury, toxic renal injury, renal tubular necrosis, renal tubular inflammation, renal tubular apoptosis, hypertension, pancreatitis, and any combination thereof.

It will be understood by one skilled in the art, based upon the disclosure provided herein, that an increase in the level of PMCA4b encompasses the increase in PMCA4b expression, including transcription, translation, or both. The skilled artisan will also appreciate, once armed with the teachings of the present invention, that an increase in the level of PMCA4b includes an increase in PMCA4b activity (e.g., enzymatic activity, substrate binding activity, etc.). Thus, increasing the level or activity of PMCA4b includes, but is not limited to, increasing the amount of PMCA4b polypeptide, and increasing transcription, translation, or both, of a nucleic acid encoding PMCA4b; and it also includes increasing any activity of a PMCA4b polypeptide as well. The PMCA4b activator compositions and methods of the invention can selectively activate PMCA4b, or can activate both PMCA4b and another molecule.

Thus, the present invention relates to the prevention and treatment of a disease or disorder by administration of a therapeutically effective amount of a PMCA4b activator composition to a subject in need thereof, for the treatment or prevention of a disease or disorder, or its associated signs, symptoms or pathologies.

It is understood by one skilled in the art, that an increase in the level of PMCA4b encompasses an increase in the amount of PMCA4b. Additionally, the skilled artisan would appreciate, that an increase in the level of PMCA4b includes an increase in PMCA4b activity. Thus, increasing the level or activity of PMCA4b includes, but is not limited to, the administration of a renalase activator, as well as increasing transcription, translation, or both, of a nucleic acid encoding PMCA4b; and it also includes increasing any activity of PMCA4b as well.

The increased level or activity of PMCA4b can be assessed using a wide variety of methods, including those disclosed herein, as well as methods well-known in the art or to be developed in the future. That is, the routineer would appreciate, based upon the disclosure provided herein, that increasing the level or activity of PMCA4b can be readily assessed using methods that assess the level of a nucleic acid encoding PMCA4b (e.g., mRNA), the level of PMCA4b polypeptide, and/or the level of PMCA4b activity in a biological sample obtained from a subject.

One skilled in the art, based upon the disclosure provided herein, would understand that the invention is useful in subjects who, in whole (e.g., systemically) or in part (e.g., locally, tissue, organ), are being or will be, treated for a disease or disorder associated with a diminished level or activity of PMCA4b. The skilled artisan will appreciate, based upon the teachings provided herein, that the diseases and disorders treatable by the compositions and methods described herein encompass any disease or disorder where in an increase in PMCA4b will promote a positive therapeutic outcome.

One of skill in the art will realize that in addition to activating PMCA4b directly, diminishing the amount or activity of a molecule that itself diminishes the amount or activity of PMCA4b can serve to increase the amount or activity of PMCA4b. Thus, a PMCA4b activator can include, but should not be construed as being limited to, a chemical compound, a protein, a peptidomemetic, an antibody, a ribozyme, an allosteric modulator, and an antisense nucleic acid molecule. One of skill in the art would readily appreciate, based on the disclosure provided herein, that a PMCA4b activator encompasses a chemical compound that increases the level, enzymatic activity, or substrate binding activity of PMCA4b. Additionally, a PMCA4b activator encompasses a chemically modified compound, fusion, conjugate, and/or derivatives, as is well known to one of skill in the chemical arts.

It will be understood by one skilled in the art, based upon the disclosure provided herein, that an increase in the level of PMCA4b encompasses the increase in PMCA4b expression, including transcription, translation, or both. The skilled artisan will also appreciate, once armed with the teachings of the present invention, that an increase in the level of PMCA4b includes an increase in PMCA4b activity (e.g., enzymatic activity, substrate binding activity, etc.). Thus, increasing the level or activity of PMCA4b includes, but is not limited to, increasing the amount of PMCA4b polypeptide, increasing transcription, translation, or both, of a nucleic acid encoding PMCA4b; and it also includes increasing any activity of a PMCA4b polypeptide as well. The PMCA4b activator compositions and methods of the invention can selectively activate PMCA4b, or can activate both PMCA4b and another molecule. Thus, the present invention relates to administration of a composition comprising a PMCA4b activator.

The PMCA4b activator compositions and methods of the invention that increase the level or activity (e.g., enzymatic activity, substrate binding activity, etc.) of PMCA4b include, but should not be construed as being limited to, a chemical compound, a protein, a peptide, a peptidomemetic, an antibody, a ribozyme, a small molecule chemical compound, an allosteric modulator, an antisense nucleic acid molecule (e.g., siRNA, miRNA, etc.), or combinations thereof. One of skill in the art would readily appreciate, based on the disclosure provided herein, that a PMCA4b activator composition encompasses a chemical compound that increases the level or activity of PMCA4b. Additionally, a PMCA4b activator composition encompasses a chemically modified compound, fusion, conjugate, and/or derivatives, as is well known to one of skill in the chemical arts.

The PMCA4b activator compositions and methods of the invention that increase the level or activity (e.g., enzymatic activity, substrate binding activity, etc.) of PMCA4b include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the antibody of the invention is an antibody that specifically binds to PMCA4b. In some embodiments, the activator is an activating renalase antibody.

In some embodiments, the activator is a renalase polypeptide, or an analogue or homolog thereof. In one embodiment, the activator is a renalase polypeptide comprising the amino acid sequence of SEQ ID NO: 8 or SEQ ID NO: 9. In another embodiment, the activator is a renalase polypeptide comprising at least a portion of the amino acid sequence of renalase. In some embodiments, the activator is a renalase polypeptide comprising the amino acid sequence of SEQ ID NO: 3, SEQ ID NO: 4, or SEQ ID NO: 5. In some embodiments, the activator is a renalase polypeptide comprising at least a portion of the amino acid sequence of SEQ ID NO: 3, SEQ ID NO: 4, or SEQ ID NO: 5. In a particular embodiment, the activator is a renalase polypeptide comprising the amino acid of SEQ ID NO: 4. In some embodiments, the renalase polypeptide, or fragment thereof, is conjugated to another molecule.

Further, one of skill in the art would, when equipped with this disclosure and the methods exemplified herein, appreciate that a PMCA4b activator includes such activators as discovered in the future, as can be identified by well-known criteria in the art of pharmacology, such as the physiological results of activation of PMCA4b as described in detail herein and/or as known in the art. Therefore, the present invention is not limited in any way to any particular PMCA4b activator as exemplified or disclosed herein; rather, the invention encompasses those activators that would be understood by the routineer to be useful as are known in the art and as are discovered in the future.

Further methods of identifying and producing a PMCA4b activator are well known to those of ordinary skill in the art, including, but not limited, obtaining an activator from a naturally occurring source (e.g., *Streptomyces* sp., *Pseudomonas* sp., *Stylotella aurantium*, etc.). Alternatively, a PMCA4b activator can be synthesized chemically. Further, the routineer would appreciate, based upon the teachings provided herein, that a PMCA4b activator can be obtained from a recombinant organism. Compositions and methods for chemically synthesizing PMCA4b activators and for obtaining them from natural sources are well known in the art and are described in the art.

One of skill in the art will appreciate that an activator can be administered as a small molecule chemical, a protein, an antibody, a nucleic acid construct encoding a protein, or combinations thereof. In some embodiments, the activator is an allosteric activator. Numerous vectors and other compositions and methods are well known for administering a protein or a nucleic acid construct encoding a protein to cells or tissues. Therefore, the invention includes a method of administering a protein or a nucleic acid encoding an protein that is an activator of PMCA4b. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of PMCA4b can serve to increase the amount or activity of PMCA4b. Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity of PMCA4b, thereby increasing the amount or activity of PMCA4b. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of PMCA4b can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that a PMCA4b activator can be administered singly or in any combination thereof. One of skill in the art will also appreciate administration can be acute (e.g., over a short period of time, such as a day, a week or a month) or chronic (e.g., over a long period of time, such as several months or a year or more). Further, a PMCA4b activator can be administered singly or in any combination thereof in a temporal sense, in that they may be administered simultaneously, before, and/or after each other. One of ordinary skill in the art will appreciate, based on the disclosure provided herein, that a PMCA4b activator can be used, and that an activator can be used alone or in any combination with another PMCA4b activator to effect a therapeutic result.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that a PMCA4b activator, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject a PMCA4b activator as a preventative measure against a disease or disorder.

As more fully discussed elsewhere herein, methods of increasing the level or activity of PMCA4b encompass a wide plethora of techniques for increasing not only PMCA4b activity, but also for increasing expression of a nucleic acid encoding PMCA4b. Additionally, as disclosed elsewhere herein, one skilled in the art would understand, once armed with the teaching provided herein, that the present invention encompasses a method of preventing a wide variety of diseases or disorders where increased expression and/or activity of PMCA4b mediates, treats or prevents a disease or disorder. Further, the invention encompasses treatment or prevention of such diseases or disorders discovered in the future.

The invention encompasses administration of a PMCA4b activator to practice the methods of the invention; the skilled artisan would understand, based on the disclosure provided herein, how to formulate and administer the appropriate PMCA4b activator to a subject. However, the present invention is not limited to any particular method of administration or treatment regimen. This is especially true where it would be appreciated by one skilled in the art, equipped with the disclosure provided herein, including the reduction to practice using an art-recognized model of ischemia-reperfusion injury, that methods of administering a PMCA4b activator can be determined by one of skill in the pharmacological arts.

As used herein, the term "pharmaceutically-acceptable carrier" means a chemical composition with which an appropriate PMCA4b modulator may be combined and which, following the combination, can be used to administer the appropriate PMCA4b modulator thereof, to a subject.

PMCA4b Inhibitor Compositions and Methods of Treatment and Prevention

In various embodiments, the present invention includes PMCA4b inhibitor compositions and methods of treating or preventing a disease or disorder where a diminished activity or level of PMCA4b is desired. One non-limiting example of a disease or disorder where a diminished activity or level of PMCA4b is desired which can be treated or prevented with the compositions and methods of the invention includes cancer. In various embodiments, the PMCA4b inhibitor compositions and methods of treatment or prevention of the invention diminish the amount of PMCA4b polypeptide, the amount of PMCA4b mRNA, the amount of PMCA4b enzymatic activity, the amount of PMCA4b substrate binding activity, or a combination thereof. In one embodiment, the PMCA4b inhibitor is caloxin 1b, or an analogue or derivative thereof. In another embodiment, the PMCA4b inhibitor is cisplatin, or an analogue or derivative thereof.

In one aspect, the methods of the present invention include a method of treating cancer in a subject in need thereof. In one embodiment, the method comprises administering to the subject a therapeutically effective amount of a composition comprising at least one PMCA4b inhibitor. In one embodiment, the cancer is selected from the group consisting of brain cancer, bladder cancer, breast cancer, cervical cancer, colorectal cancer, liver cancer, kidney cancer, lymphoma, leukemia, lung cancer, melanoma, metastatic melanoma, mesothelioma, neuroblastoma, ovarian cancer, prostate cancer, pancreatic cancer, renal cancer, skin cancer, thymoma, sarcoma, non-Hodgkin's lymphoma, Hodgkin's lymphoma, uterine cancer, and any combination thereof.

It will be understood by one skilled in the art, based upon the disclosure provided herein, that a decrease in the level of PMCA4b encompasses the decrease in PMCA4b expression, including transcription, translation, or both. The skilled artisan will also appreciate, once armed with the teachings of the present invention, that a decrease in the level of PMCA4b includes a decrease in PMCA4b activity (e.g., enzymatic activity, substrate binding activity, etc.). Thus, decreasing the level or activity of PMCA4b includes, but is not limited to, decreasing transcription, translation, or both, of a nucleic acid encoding PMCA4b; and it also includes decreasing any activity of a PMCA4b polypeptide as well. The PMCA4b inhibitor compositions and methods of the invention can selectively inhibit PMCA4b, or can inhibit both PMCA4b and another molecule.

Inhibition of PMCA4b can be assessed using a wide variety of methods, including those disclosed herein, as well as methods known in the art or to be developed in the future. That is, the routineer would appreciate, based upon the disclosure provided herein, that decreasing the level or activity of PMCA4b can be readily assessed using methods that assess the level of a nucleic acid encoding PMCA4b (e.g., mRNA), the level of a PMCA4b polypeptide present in a biological sample, the level of PMCA4b activity (e.g., enzymatic activity, substrate binding activity, etc.), or combinations thereof.

One skilled in the art, based upon the disclosure provided herein, would understand that the invention is useful in treating or preventing in a subject in need thereof, whether or not the subject is also being treated with other medication or therapy. Further, the skilled artisan would further appreciate, based upon the teachings provided herein, that the disease or disorders treatable by the compositions and methods described herein encompass any disease or disorder where PMCA4b plays a role and where diminished PMCA4b level or activity will promote a positive therapeutic outcome.

The PMCA4b inhibitor compositions and methods of the invention that decrease the level or activity (e.g., enzymatic activity, substrate binding activity, etc.) of PMCA4b include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof. In some embodiments, the inhibitor is an allosteric inhibitor. One of skill in the art would readily appreciate, based on the disclosure provided herein, that a PMCA4b inhibitor composition encompasses a chemical compound that decreases the level or activity of PMCA4b. Additionally, a PMCA4b inhibitor composition encompasses a chemically modified compound, and derivatives, as is well known to one of skill in the chemical arts.

The PMCA4b inhibitor compositions and methods of the invention that decrease the level or activity (e.g., enzymatic activity, substrate binding activity, etc.) of PMCA4b include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the antibody of the invention is an antibody that specifically binds to PMCA4b.

Further, one of skill in the art, when equipped with this disclosure and the methods exemplified herein, would appreciate that a PMCA4b inhibitor composition includes such inhibitors as discovered in the future, as can be identified by well-known criteria in the art of pharmacology, such as the physiological results of inhibition of PMCA4b as described in detail herein and/or as known in the art. Therefore, the present invention is not limited in any way to any particular PMCA4b inhibitor composition as exemplified or disclosed herein; rather, the invention encompasses those inhibitor compositions that would be understood by the routineer to be useful as are known in the art and as are discovered in the future.

Further methods of identifying and producing PMCA4b inhibitor compositions are well known to those of ordinary skill in the art, including, but not limited, obtaining an inhibitor from a naturally occurring source (e.g., *Streptomyces* sp., *Pseudomonas* sp., *Stylotella aurantium*, etc.). Alternatively, a PMCA4b inhibitor can be synthesized chemically. Further, the routineer would appreciate, based upon the teachings provided herein, that a PMCA4b inhibitor composition can be obtained from a recombinant organism. Compositions and methods for chemically synthesizing PMCA4b inhibitors and for obtaining them from natural sources are well known in the art and are described in the art.

One of skill in the art will appreciate that an inhibitor can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of PMCA4b. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the amount or activity of PMCA4b can serve in the compositions and methods of the present invention to decrease the amount or activity of PMCA4b.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of PMCA4b, or to diminish the amount of a molecule that causes an increase in the amount or activity of PMCA4b, thereby decreasing the amount or activity of PMCA4b.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing PMCA4b, or of a gene expressing a protein that increases the level or activity of PMCA4b, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168, 053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that inhibitors of PMCA4b can be administered acutely (e.g., over a short period of time, such as a day, a week or a month) or chronically (e.g., over a long period of time, such as several months or a year or more). One of skill in the art will appreciate that inhibitors of PMCA4b can be administered singly or in any combination with other agents. Further, PMCA4b inhibitors can be administered singly or in any combination in a temporal sense, in that they may be administered concurrently, or before, and/or after each other. One of ordinary skill in the art will appreciate, based on the disclosure provided herein, that PMCA4b inhibitor compositions can be used to treat or prevent a disease or disorder in a subject in need thereof, and that an inhibitor composition can be used alone or in any combination with another inhibitor to effect a therapeutic result.

In various embodiments, any of the inhibitors of PMCA4b of the invention described herein can be administered alone or in combination with other inhibitors of other molecules associated with cancer.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that a PMCA4b inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject a PMCA4b inhibitor composition as a preventative measure against the disease or disorder. As more fully discussed elsewhere herein, methods of decreasing the level or activity of PMCA4b encompass a wide plethora of techniques for decreasing not only PMCA4b activity, but also for decreasing expression of a nucleic acid encoding PMCA4b, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of PMCA4b mediates, treats or prevents the disease, disorder or pathology. Methods for assessing whether a disease relates to the levels or activity of PMCA4b are known in the art. Further, the invention encompasses treatment or prevention of such diseases discovered in the future.

The invention encompasses administration of an inhibitor of PMCA4b to practice the methods of the invention; the skilled artisan would understand, based on the disclosure provided herein, how to formulate and administer the appropriate PMCA4b inhibitor to a subject. However, the present invention is not limited to any particular method of administration or treatment regimen.

Methods of Identifying a Modulator of a Renalase Receptor

The current invention relates to a methods of identifying a compound that modulates the activity of a renalase receptor, such as, for example, PMCA4b. In some embodiments, the method of identifying of the invention identifies an inhibitor compound that decreases the activity of a renalase receptor, such as, for example, PMCA4b. In other embodiments, the method of identifying of the invention identifies an activator compound that increases the activity of a renalase receptor, such as, for example, PMCA4b.

Other methods, as well as variation of the methods disclosed herein will be apparent from the description of this invention. In various embodiments, the test compound concentration in the screening assay can be fixed or varied. A single test compound, or a plurality of test compounds, can be tested at one time. In some embodiments, the method of identifying is a high-throughput screen. Suitable test compounds that may be used include, but are not limited to, proteins, nucleic acids, antisense nucleic acids, shRNA, small molecules, antibodies and peptides.

The invention relates to a method for screening test compounds to identify a modulator compound by its ability to modulate (i.e., increase or decrease) the level of activity of a renalase receptor, such as, for example, PMCA4b, in the presence and absence of the test compound. The activity of the renalase receptor that is assessed can be any measurable activity of the renalase receptor. In one embodiment, the activity of the renalase receptor that is assessed is the level of mitogen-activated protein kinase (MAPK) signaling. In another embodiment, the activity of the renalase receptor that is assessed is the level of ATPase activity.

Test compounds that can be assessed in the methods of the invention include a chemical compound, a protein, a peptide, a peptidomemetic, an antibody, a nucleic acid, an antisense nucleic acid, an siRNA, a miRNA, a shRNA, a ribozyme, an allosteric modulator, and a small molecule chemical compound.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223, 409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical to that new chemical entities with useful properties are generated by identifying a chemical compound (called a "lead compound") with some desirable property or activity, creating variants of the lead compound, and evaluating the property and activity of those variant compounds.

In one embodiment, high throughput screening methods involve providing a library containing a large number of test compounds potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Compositions and Methods of Treatment and Prevention

In various embodiments, the present invention includes renalase activator compositions and methods of increasing the level or activity of renalase, or a fragment thereof, in a subject, a tissue, or an organ in need thereof. In various embodiments, the renalase activator compositions and methods of treatment of the invention increase the amount of renalase polypeptide, the amount of renalase mRNA, the amount of renalase enzymatic activity, the amount of renalase substrate binding activity, or a combination thereof. In various embodiments, the diseases and disorders where in increase in renalase may improve therapeutic outcome include, but are not limited to, pancreatic diseases or disorders such as pancreatitis.

It will be understood by one skilled in the art, based upon the disclosure provided herein, that an increase in the level of renalase encompasses the increase in renalase expression, including transcription, translation, or both. The skilled artisan will also appreciate, once armed with the teachings of the present invention, that an increase in the level of renalase includes an increase in renalase activity (e.g., enzymatic activity, substrate binding activity, etc.). Thus, increasing the level or activity of renalase includes, but is not limited to, increasing the amount of renalase polypeptide, and increasing transcription, translation, or both, of a nucleic acid encoding renalase; and it also includes increasing any activity of a renalase polypeptide as well. The renalase activator compositions and methods of the invention can selectively activate renalase, or can activate both renalase and another molecule.

Thus, the present invention relates to the prevention and treatment of a disease or disorder by administration of a therapeutically effective amount of a renalase polypeptide, a recombinant renalase polypeptide, an active renalase polypeptide fragment (i.e., renalase peptide), or an activator of renalase expression or activity, to a subject in need thereof, for the treatment or prevention of a disease or disorder, or its associated signs, symptoms or pathologies. In some embodiments, the renalase polypeptide comprises the amino acid of SEQ ID NO: 8 or SEQ ID NO: 9, or an analogue or homolog thereof. In some embodiments, the renalase of the invention is a renalase polypeptide fragment comprising at least a portion of the amino acid sequence of SEQ ID NO: 8 or SEQ ID NO: 9, or an analogue or homolog thereof. In some embodiments, the renalase polypeptide fragment is a peptide that retains its protective activity, but does not exhibit detectable NADH oxidase activity. In some embodiments, the renalase polypeptide fragment is a peptide that retains its protective activity, but does not exhibit detectable amine oxidase activity. In a particular embodiment, the renalase polypeptide fragment is a peptide comprising the amino acid sequence of SEQ ID NO: 3, or an analogue or homolog thereof. In another particular embodiment, the renalase polypeptide fragment is a peptide comprising the amino acid sequence of SEQ ID NO: 4, or an analogue or homolog thereof. In another particular embodiment, the renalase polypeptide fragment is a peptide comprising the amino acid sequence of SEQ ID NO: 5, or an analogue or homolog thereof. In another particular embodiment, the renalase polypeptide fragment is a peptide consisting of the amino acid sequence of SEQ ID NO: 3, or an analogue or homolog thereof. In another particular embodiment, the renalase polypeptide fragment is a peptide consisting of the amino acid sequence of SEQ ID NO: 4, or an analogue or homolog thereof. In another particular embodiment, the renalase polypeptide fragment is a peptide consisting of the amino acid sequence of SEQ ID NO: 5, or an analogue or homolog thereof. In some embodiments, the renalase polypeptide, or fragment thereof, is conjugated to another molecule.

It is understood by one skilled in the art, that an increase in the level of renalase encompasses an increase in the amount of renalase, or fragment thereof (e.g., by administration of renalase or a fragment thereof, by increasing renalase protein expression, etc.). Additionally, the skilled artisan would appreciate, that an increase in the level of renalase includes an increase in renalase activity. Thus, increasing the level or activity of renalase includes, but is not limited to, the administration of renalase or a fragment thereof, as well as increasing transcription, translation, or both, of a nucleic acid encoding renalase; and it also includes increasing any activity of renalase as well.

The increased level or activity of renalase can be assessed using a wide variety of methods, including those disclosed herein, as well as methods well-known in the art or to be developed in the future. That is, the routineer would appreciate, based upon the disclosure provided herein, that increasing the level or activity of renalase can be readily assessed using methods that assess the level of a nucleic acid encoding renalase (e.g., mRNA), the level of renalase polypeptide, and/or the level of renalase activity in a biological sample obtained from a subject.

One skilled in the art, based upon the disclosure provided herein, would understand that the invention is useful in subjects who, in whole (e.g., systemically) or in part (e.g., locally, tissue, organ), are being or will be, treated for a disease or disorder associated with a diminished level or activity of renalase. The skilled artisan will appreciate, based upon the teachings provided herein, that the diseases and disorders treatable by the compositions and methods described herein encompass any disease or disorder where in an increase in renalase will promote a positive therapeutic outcome.

One of skill in the art will realize that in addition to activating renalase directly, diminishing the amount or activity of a molecule that itself diminishes the amount or activity of renalase can serve to increase the amount or activity of renalase. Thus, a renalase activator can include, but should not be construed as being limited to, a chemical compound, a protein, a peptidomemetic, an antibody, a ribozyme, and an antisense nucleic acid molecule. In some embodiments the renalase activator is an allosteric activator. One of skill in the art would readily appreciate, based on the disclosure provided herein, that a renalase activator encompasses a chemical compound that increases the level, enzymatic activity, or substrate binding activity of renalase. Additionally, a renalase activator encompasses a chemically modified compound, and derivatives, as is well known to one of skill in the chemical arts.

It will be understood by one skilled in the art, based upon the disclosure provided herein, that an increase in the level of renalase encompasses the increase in renalase expression, including transcription, translation, or both. The skilled artisan will also appreciate, once armed with the teachings of the present invention, that an increase in the level of renalase includes an increase in renalase activity (e.g., enzymatic activity, substrate binding activity, etc.). Thus, increasing the level or activity of renalase includes, but is not limited to, increasing the amount of renalase polypeptide, increasing transcription, translation, or both, of a nucleic acid encoding renalase; and it also includes increasing any activity of a renalase polypeptide as well. The renalase activator compositions and methods of the invention can selectively activate renalase, or can activate both renalase and another molecule. Thus, the present invention relates to administration of a renalase polypeptide, a recombinant renalase polypeptide, an active renalase polypeptide fragment, or an activator of renalase expression or activity.

Further, one of skill in the art would, when equipped with this disclosure and the methods exemplified herein, appreciate that a renalase activator includes such activators as discovered in the future, as can be identified by well-known criteria in the art of pharmacology, such as the physiological results of activation of renalase as described in detail herein and/or as known in the art. Therefore, the present invention is not limited in any way to any particular renalase activator as exemplified or disclosed herein; rather, the invention encompasses those activators that would be understood by the routineer to be useful as are known in the art and as are discovered in the future.

Further methods of identifying and producing a renalase activator are well known to those of ordinary skill in the art, including, but not limited, obtaining an activator from a naturally occurring source (e.g., *Streptomyces* sp., *Pseudomonas* sp., *Stylotella aurantium*, etc.). Alternatively, a renalase activator can be synthesized chemically. Further, the routineer would appreciate, based upon the teachings provided herein, that a renalase activator can be obtained from a recombinant organism. Compositions and methods for chemically synthesizing renalase activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an activator of renalase. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of renalase can serve to increase the amount or activity of renalase. Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190, 931). The methods of the invention include the use of antisense oligonucleotide to diminish the amount of a molecule that causes a decrease in the amount or activity renalase, thereby increasing the amount or activity of renalase. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of renalase can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that a renalase activator, renalase polypeptide, a recombinant renalase polypeptide, or an active renalase polypeptide fragment can be administered singly or in any combination thereof. One of skill in the art will also appreciate administration can be acute (e.g., over a short period of time, such as a day, a week or a month) or chronic (e.g., over a long period of time, such as several months or a year or more). Further, a renalase polypeptide, a recombinant renalase polypeptide, or an active renalase polypeptide fragment can be administered singly or in any combination thereof in a temporal sense, in that they may be administered simultaneously, before, and/ or after each other. One of ordinary skill in the art will appreciate, based on the disclosure provided herein, that a renalase polypeptide, a recombinant renalase polypeptide, or an active renalase polypeptide fragment can be used, and that an activator can be used alone or in any combination with another renalase polypeptide, recombinant renalase polypeptide, active renalase polypeptide fragment, or renalase activator to effect a therapeutic result. One of ordinary skill in the art will also appreciate, based on the disclosure provided herein, that a renalase polypeptide, a recombinant renalase polypeptide, or an active renalase polypeptide fragment can be can be used alone or in any combination with any other composition, drug, or treatment useful in treating a pancreatic disease or disorder, such as pancreatitis. In some embodiments, the administered renalase polypeptide, recombinant renalase polypeptide, active renalase polypeptide fragment, or combinations thereof, are administered in combination with another composition, drug, or treatment that reduces, inhibits, or blocks the metabolism or degradation of the administered renalase polypeptide, recombinant renalase polypeptide, active renalase polypeptide fragment, or combination thereof.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that a renalase molecule (e.g., polypeptide, peptide, etc.), or a renalase activator, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject a renalase polypeptide, a recombinant renalase polypeptide, an active renalase polypeptide fragment, or renalase activator as a preventative measure against a disease or disorder.

As more fully discussed elsewhere herein, methods of increasing the level or activity of a renalase encompass a wide plethora of techniques for increasing not only renalase activity, but also for increasing expression of a nucleic acid encoding renalase. Additionally, as disclosed elsewhere herein, one skilled in the art would understand, once armed with the teaching provided herein, that the present invention encompasses a method of preventing a wide variety of diseases or disorders where increased expression and/or activity of renalase mediates, treats or prevents a disease or disorder. Further, the invention encompasses treatment or prevention of such diseases or disorders discovered in the future.

The invention encompasses administration of a renalase polypeptide, a recombinant renalase polypeptide, an active renalase polypeptide fragment, or a renalase activator to practice the methods of the invention; the skilled artisan would understand, based on the disclosure provided herein, how to formulate and administer the appropriate renalase polypeptide, recombinant renalase polypeptide, active renalase polypeptide fragment, or renalase activator to a subject. However, the present invention is not limited to any particular method of administration or treatment regimen. This is especially true where it would be appreciated by one skilled in the art, equipped with the disclosure provided herein, including the reduction to practice using an art-recognized model of ischemia-reperfusion injury, that methods of administering a renalase polypeptide, a recombinant renalase polypeptide, an active renalase polypeptide fragment, or renalase activator can be determined by one of skill in the pharmacological arts.

As used herein, the term "pharmaceutically-acceptable carrier" means a chemical composition with which an appropriate renalase modulator may be combined and which, following the combination, can be used to administer the appropriate renalase modulator thereof, to a subject.

Methods of Diagnosis

In some embodiments, a change (i.e., increase or decrease) in the level of renalase compared with a comparator is used in the methods of the invention as marker for the diagnosis of a pancreatic disease or disorder, as well as for monitoring the treatment the effectiveness of a pancreatic disease or disorder.

In one embodiment, the invention is a method of diagnosing a pancreatic disease or disorder of a subject by assessing the level of renalase in a biological sample of the subject. In one embodiment, the biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of monitoring the progression of a pancreatic disease or disorder of a subject by assessing the level of renalase in a biological sample of the subject. In one embodiment, the biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In a further embodiment, the invention is a method of assessing the severity of a pancreatic disease or disorder of a subject by assessing the level of renalase in a biological sample of the subject. In one embodiment, the biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of selecting a treatment regimen to treat a pancreatic disease or disorder of a subject by assessing the level of renalase in a biological sample of the subject. In one embodiment biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of monitoring the effect of a treatment of a pancreatic disease or disorder of a subject by assessing the level of renalase in a biological sample of the subject. In one embodiment, the biological sample of the subject is a bodily fluid. Non-limiting examples of bodily fluids in which the level of renalase can be assessed include, but are not limited to, blood, serum, plasma and urine. In various embodiments, the level of renalase in the biological sample of the subject is compared with the renalase level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In various embodiments, the subject is a human subject, and may be of any race, sex and age. Representative subjects include those who are suspected of having experienced a pancreatic disease or disorder, such as pancreatitis, those who have been diagnosed as having experienced a pancreatic disease or disorder, such as pancreatitis, those who have been diagnosed as having a disease or disorder associated with a pancreatic disease or disorder, and those who are at risk of developing a pancreatic disease or disorder, such as pancreatitis.

Information obtained from the methods of the invention described herein can be used alone, or in combination with other information (e.g., disease status, disease history, vital signs, blood chemistry, etc.) from the subject or from the biological sample obtained from the subject.

In the diagnostic methods of the invention, a biological sample obtained from a subject is assessed for the level of renalase contained therein. In one embodiment, the biological sample is a sample containing at least a fragment of a renalase polypeptide useful in the methods described herein.

In other various embodiments of the methods of the invention, the level of renalase is determined to be reduced when the level of renalase is reduced by at least 10%, by at least 20%, by at least 30%, by at least 40%, by at least 50%, by at least 60%, by at least 70%, by at least 80%, by at least 90%, or by at least 100%, when compared to with a comparator control. In various embodiments, a reduced level of renalase is indicative of a disease or disorder.

In other various embodiments of the methods of the invention, the level of renalase is determined to be increased when the level of renalase is increased by at least 10%, by at least 20%, by at least 30%, by at least 40%, by at least 50%, by at least 60%, by at least 70%, by at least 80%, by at least 90%, or by at least 100%, when compared to with a comparator control. In various embodiments, an increased level of renalase is indicative of a disease or disorder.

In the methods of the invention, a biological sample from a subject is assessed for the level of renalase in the biological sample obtained from the patient. The level of renalase in the biological sample can be determined by assessing the amount of renalase polypeptide in the biological sample, the amount of renalase mRNA in the biological sample, the amount of renalase enzymatic activity in the biological sample, or a combination thereof.

In various embodiments of the methods of the invention, methods of measuring renalase levels in a biological sample obtained from a patient include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (MA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

Therapeutic Inhibitor Compositions and Methods

In various embodiments, the present invention includes renalase inhibitor compositions and methods of treating or preventing a disease or disorder where a diminished activity or level of renalase is desired. One non-limiting example of a disease or disorder where a diminished activity or level of renalase is desired which can be treated or prevented with the compositions and methods of the invention includes cancer. In various embodiments, the renalase inhibitor compositions and methods of treatment or prevention of the invention diminish the amount of renalase polypeptide, the amount of renalase mRNA, the amount of renalase enzymatic activity, the amount of renalase substrate binding activity, or a combination thereof.

It will be understood by one skilled in the art, based upon the disclosure provided herein, that a decrease in the level of renalase encompasses the decrease in renalase expression, including transcription, translation, or both. The skilled artisan will also appreciate, once armed with the teachings of the present invention, that a decrease in the level of renalase includes a decrease in renalase activity (e.g., enzymatic activity, substrate binding activity, etc.). Thus, decreasing the level or activity of renalase includes, but is not limited to, decreasing transcription, translation, or both, of a nucleic acid encoding renalase; and it also includes decreasing any activity of a renalase polypeptide as well. The renalase inhibitor compositions and methods of the invention can selectively inhibit renalase, or can inhibit both renalase and another molecule.

Inhibition of renalase can be assessed using a wide variety of methods, including those disclosed herein, as well as methods known in the art or to be developed in the future. That is, the routineer would appreciate, based upon the disclosure provided herein, that decreasing the level or activity of renalase can be readily assessed using methods that assess the level of a nucleic acid encoding renalase (e.g., mRNA), the level of a renalase polypeptide present in a biological sample, the level of renalase activity (e.g., enzymatic activity, substrate binding activity, etc.), or combinations thereof.

One skilled in the art, based upon the disclosure provided herein, would understand that the invention is useful in treating or preventing in a subject in need thereof, whether or not the subject is also being treated with other medication or therapy. Further, the skilled artisan would further appreciate, based upon the teachings provided herein, that the disease or disorders treatable by the compositions and methods described herein encompass any disease or disorder where renalase plays a role and where diminished renalase level or activity will promote a positive therapeutic outcome.

The renalase inhibitor compositions and methods of the invention that decrease the level or activity (e.g., enzymatic activity, substrate binding activity, etc.) of renalase include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof. In some embodiments, the inhibitor is an allosteric inhibitor. One of skill in the art would readily appreciate, based on the disclosure provided herein, that a renalase inhibitor composition encompasses a chemical compound that decreases the level or activity of renalase. Additionally, a renalase inhibitor composition encompasses a chemically modified compound, and derivatives, as is well known to one of skill in the chemical arts.

The renalase inhibitor compositions and methods of the invention that decrease the level or activity (e.g., enzymatic activity, substrate binding activity, etc.) of renalase include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and a humanized antibodies. In one embodiment, the antibody of the invention is an antibody that specifically binds to renalase.

Further, one of skill in the art, when equipped with this disclosure and the methods exemplified herein, would appreciate that a renalase inhibitor composition includes such inhibitors as discovered in the future, as can be identified by well-known criteria in the art of pharmacology, such as the physiological results of inhibition of renalase as described in detail herein and/or as known in the art. Therefore, the present invention is not limited in any way to any particular renalase inhibitor composition as exemplified or disclosed herein; rather, the invention encompasses those inhibitor compositions that would be understood by the routineer to be useful as are known in the art and as are discovered in the future.

Further methods of identifying and producing renalase inhibitor compositions are well known to those of ordinary skill in the art, including, but not limited, obtaining an inhibitor from a naturally occurring source (e.g., *Streptomyces* sp., *Pseudomonas* sp., *Stylotella aurantium*, etc.). Alternatively, a renalase inhibitor can be synthesized chemically. Further, the routineer would appreciate, based upon the teachings provided herein, that a renalase inhibitor composition can be obtained from a recombinant organism. Compositions and methods for chemically synthesizing renalase inhibitors and for obtaining them from natural sources are well known in the art and are described in the art.

One of skill in the art will appreciate that an inhibitor can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of renalase. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the amount or activity of renalase can serve in the compositions and methods of the present invention to decrease the amount or activity of renalase.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of renalase, or to diminish the amount of a molecule that causes an increase in the amount or activity of renalase, thereby decreasing the amount or activity of renalase.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing renalase, or of a gene expressing a protein that increases the level or activity of renalase, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that inhibitors of renalase can be administered acutely (e.g., over a short period of time, such as a day, a week or a month) or chronically (e.g., over a long period of time, such as several months or a year or more). One of skill in the art will appreciate that inhibitors of renalase can be administered singly or in any combination with other agents. Further, renalase inhibitors can be administered singly or in any combination in a temporal sense, in that they may be administered concurrently, or before, and/or after each other. One of ordinary skill in the art will appreciate, based on the disclosure provided herein, that renalase inhibitor compositions can be used to treat or prevent a disease or disorder in a subject in need thereof, and that an inhibitor composition can be used alone or in any combination with another inhibitor to effect a therapeutic result.

In various embodiments, any of the inhibitors of renalase of the invention described herein can be administered alone or in combination with other inhibitors of other molecules associated with cancer.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that a renalase inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject a renalase inhibitor composition as a preventative measure against the disease or disorder. As more fully discussed elsewhere herein, methods of decreasing the level or activity of renalase encompass a wide plethora of techniques for decreasing not only renalase activity, but also for decreasing expression of a nucleic acid encoding renalase, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of renalase mediates, treats or prevents the disease, disorder or pathology. Methods for assessing whether a disease relates to the levels or activity of renalase are known in the art. Further, the invention encompasses treatment or prevention of such diseases discovered in the future.

The invention encompasses administration of an inhibitor of renalase to practice the methods of the invention; the skilled artisan would understand, based on the disclosure provided herein, how to formulate and administer the appropriate renalase inhibitor to a subject. However, the present invention is not limited to any particular method of administration or treatment regimen.

Kits

The present invention also pertains to kits useful in the methods of the invention. Such kits comprise various combinations of components useful in any of the methods described elsewhere herein, including for example, a PMCA4b modulator, a renalase activator, a renalase inhibitor, materials for quantitatively analyzing renalase polypeptide or renalase nucleic acid, materials for assessing the activity of a renalase polypeptide or a renalase nucleic acid, and instructional material. For example, in one embodiment, the kit comprises components useful for the quantification of renalase nucleic acid in a biological sample. In another embodiment, the kit comprises components useful for the quantification of renalase polypeptide in a biological sample. In a further embodiment, the kit comprises components useful for the assessment of the activity (e.g., enzymatic activity, substrate binding activity, etc.) of a renalase polypeptide in a biological sample.

In a further embodiment, the kit comprises the components of method for diagnosing a disease or disorder, or for monitoring the effectiveness of a treatment administered to a subject in need thereof, containing instructional material and the components for determining whether the level of renalase in a biological sample obtained from the subject is modulated during or after administration of the treatment. In various embodiments, to determine whether the level of renalase is modulated in a biological sample obtained from the subject, the level of renalase is compared with the level of at least one comparator control contained in the kit, such as a positive control, a negative control, a historical control, a historical norm, or the level of another reference molecule in the biological sample. In certain embodiments, the ratio of renalase and a reference molecule is determined to aid in the monitoring of the treatment.

Pharmaceutical Compositions and Administration

Compositions comprising a PMCA4b modulator can be formulated and administered to a subject, as now described. In one embodiment, the PMCA4b modulator is a PMCA4b activator. In another embodiment, the PMCA4b modulator is a PMCA4b inhibitor. For example, compositions identified as useful PMCA4b modulators for the treatment and/or prevention of a disease or disorder can be formulated and administered to a subject, as now described.

Compositions comprising a renalase polypeptide, a renalase polypeptide fragment, an activator of renalase level or activity, or an inhibitor of renalase level or activity can be formulated and administered to a subject, as now described. By way of non-limiting examples, a composition identified as a useful renalase active or activator, including renalase polypeptides, recombinant renalase polypeptides, and active renalase polypeptide fragments, for the treatment and/or prevention of a disease or disorder can be formulated and administered to a subject, as now described. By way of more non-limiting examples, a composition identified as a useful renalase inhibitor, including a chemical compound, a protein, a peptide, a peptidomemetic, an antibody, a ribozyme, a small molecule chemical compound, an antisense nucleic acid molecule (e.g., siRNA, miRNA, etc.), for the treatment and/or prevention of a disease or disorder can be formulated and administered to a subject, as now described.

The invention encompasses the preparation and use of pharmaceutical compositions comprising a composition useful for the treatment or prevention of a disease or disorder, disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. In various embodiments, the active ingredient is a PMCA4b modulator, as elsewhere described herein.

As used herein, the term "pharmaceutically-acceptable carrier" means a chemical composition with which an appropriate PMCA4b modulator thereof, may be combined and which, following the combination, can be used to administer the appropriate PMCA4b modulator thereof, to a subject.

The pharmaceutical compositions useful for practicing the invention may be administered to deliver a dose of between about 0.1 ng/kg/day and 100 mg/kg/day, or more.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate modulator thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, transdermal, subcutaneous, intramuscular, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

Pharmaceutically acceptable excipients used in the manufacture of pharmaceutical compositions include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Liquid formulations of a pharmaceutical composition of the invention may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference. Typically dosages of the compound of the invention which may be administered to an animal, preferably a human, range in amount from about 0.01 mg to about 1000 mg per kilogram of body weight of the animal. The precise dosage administered will vary depending upon any number of factors, including, but not limited to, the type of animal and type of disease or disorder being treated, the age of the animal and the route of administration. Preferably, the dosage of the compound will vary from about 1 mg to about 100 mg per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease or disorder being treated, the type and age of the animal, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Identification of a Receptor for Extracellular Renalase

The results described herein identify PMCA4b as a renalase receptor, and a key mediator of renalase dependent MAPK signaling. Using biotin transfer studies with RP-220 in the human proximal tubular cell line HK-2 and protein identification by mass spectrometry, PMCA4b was identified as a renalase binding protein. This previously characterized plasma membrane ATPase is involved in cell signaling and cardiac hypertrophy. Co-immunoprecipitation and co-immunolocalization confirmed protein-protein interaction between endogenous renalase and PMCA4b. Downregulation of endogenous PMCA4b expression by siRNA transfection, or inhibition of its enzymatic activity by the specific peptide inhibitor caloxin1b each abrogated RP-220 dependent MAPK signaling and cytoprotection. In control studies, these maneuvers had no effect on epidermal growth factor mediated signaling, confirming specificity of the interaction between PMCA4b and renalase.

The materials and methods employed in these experiments are now described.

Materials and Methods

Synthesis and Analysis of Renalase and Renalase Peptides

Renalase peptides (SEQ ID NOs 1-7; FIG. 1A) were acetylated at the amino terminus and purified to 98% homogeneity (United Peptides, Herndon, Va.). Recombinant renalase was synthesized as previously described (Desir et al., 2012, J. Am. Heart Assoc. 1:e002634). Renalase expression was detected using an anti-renalase monoclonal antibody generated against the renalase peptide RP-220 (amino acid 220-239 of hRenalase1; SEQ ID NO: 4)

Renalase Receptor Cross Linking and Identification

Potential disulfide bonds formed by the single, amino terminal cysteine present in renalase peptide 220 (RP-220; SEQ ID NO: 4), and in the scrambled renalase peptide (RP-Scr220, control peptide; SEQ ID NO: 7) (FIG. 1A) were disrupted using an immobilized reducing column (#77701, Pierce Biotechnology, Rockford, Ill.). The reduced peptides were recovered by elution, and the concentration of free sulfhydryl groups was estimated using the Ellman's Reagent (#22582, Pierce Biotechnology, Rockford, Ill.).

Reduced RP-220 (SEQ ID NO: 4) and RP-Scr220 (SEQ ID NO: 7) were conjugated to a tri-functional cross-linker, Mts-Atf-Biotin (#33093, Pierce Biotechnology, Rockford, Ill.) according to the manufacturer's instructions. Conjugation was achieved through the sulfhydryl-reactive methanethiosulfonate (Mts) moiety, and the spacer arm between Mts, and the photoactivatable tetrafluorophenyl azide (Atf) moiety was 11 Å. Coupling efficiency was estimated by dot blot using streptavidin-HRP to measure biotin incorporation (#21130, Pierce Biotechnology, Rockford, Ill.). The labeled probes were protected from light and stored in 50 µl aliquots, at −80° C. until use.

HK-2 cells (human proximal tubular cell line), obtained from American Type Culture Collection (ATCC, Manassas, Va.) were grown at 37° C. to 80% confluence in 150 mm dishes in DMEM/F12 media supplemented with glutamine, 10% FBS, antibiotics, and 5% $CO_2$. Cells were cooled to 4° C. to prevent probe internalization, and then incubated for 16 hrs with 50 µg of either Mts-Atf-Biotin labeled RP220 or RP-Scr220. Cross-linking of the probes was initiated by exposing the cells to ultraviolet light for five minutes using a Stratalinker 2500 (Stratagene, Agilent Technologies, Santa Clara, Calif.).

The cells were suspended in phosphate buffered saline (PBS) with protease inhibitors (Complete Ultra #05892953001, Roche Diagnostics, Indianapolis, Ind.) and subjected to 3 cycles of freeze-thawing. The membrane fraction was collected by centrifugation (180,000 g for 1 hour) and solubilized in RIPA buffer (20 mM Tris-HCl pH 7.5, 150 mM NaCl, 1 mM $Na_2EDTA$, 1 mM EGTA, 1% NP-40, 1% sodium deoxycholate, 2.5 mM sodium pyrophosphate, 1 mM glycerophosphate, 1 mM $Na_3VO_4$, 1 µg/ml leupeptin) (Cell Signaling Technologies, Danvers, Mass.) for 4 hours at 4° C.

The biotinylated proteins were purified using streptavidin agarose resin (Pierce Biotechnology, Rockford, Ill.) according to the manufacturer's instructions. The proteins were separated by SDS PAGE using a 4-20% gradient gel (Bio-Rad, Hercules, Calif.) and stained by Western-blotting using streptavidin-HRP to identify proteins bands found predominantly cross-linked to the renalase bait RP-220. These bands and the corresponding bands from the samples cross-linked to the control bait RP-Scr220 were cut out of coomassie blue stained gels, and individual proteins were identified by mass spectrometry (Yale Keck Biotechnology Resource Laboratory). Plasma membrane protein(s) consistently present in the samples cross-linked to RP-220, and absent from those cross-linked to the control bait RP-Scr220 were evaluated further.

Downregulation of PMCA4b Expression Using siRNA

ATP2B4 (PMCA4b) specific siRNAs and non-targeting controls (SMARTpool ON-TARGETplus ATP2B4 siRNA, L-006118-00-0005) were purchased from Thermo Fischer Scientific (Waltham, Mass.), and transfected into HK-2 cells using Lipofectamine 2000 (Invitrogen, Life Technologies Grand Island N.Y.). HK-2 cells were grown to 70% confluence in DMEM/F12 medium supplemented with 10% FBS. PMCA4b protein expression was assessed by western immunoblot using an anti-PMCA4 mouse monoclonal antibody (# H00000493-M07, Novus Biologicals, Littleton, Colo.).

Detection of Endogenous Co-Expression of PMCA4b and Renalase

HK-2 cells, which highly express renalase and PMCA4b endogenously, were fixed, permeabilized, and incubated with a goat polyclonal anti-renalase antibody (# AF5350, R&D Systems, Minneapolis, Minn.), and an anti-PMCA4 mouse monoclonal antibody (# H00000493-M07, Novus Biologicals, Littleton, Colo.) for 2 hours at room temperature. Following the application of two labeled secondary antibodies (Alexa488-rabbit anti-goat to detect renalase and Alexa555-goat anti-mouse to detect PMCA4, Molecular Probes, Life Technologies Grand Island N.Y.), cells were then examined using a Zeiss LSM 510 confocal imaging system.

Co-Immunoprecipitation of Endogenous PMCA4b and Renalase

HK-2 cells were lysed using ice-cold RIPA buffer (Cell Signaling Technologies, Danvers, Mass.), and the lysate was centrifuged 14,000 g for 15 min. The supernatant was collected and incubated with protein A/G agarose beads (Santa Cruz Biotechnology, Santa Cruz, Calif.) to reduce non-specific binding. Immunoprecipitation was carried out using A/G agarose beads and either goat polyclonal anti-renalase antibody or anti-PMCA4 mouse monoclonal antibody, and proteins were visualized by western blotting.

Gene Expression Analysis

Total RNA from tissue samples was extracted using RNeasy Plus kit (Qiagen, Valencia, Calif.) and converted into cDNA using an Omniscript RT kit (Qiagen, Valencia, Calif.). PMCA4b mRNA in kidney was assessed in renalase KO mice by real-time PCR and normalized to the corresponding levels in WT samples (defined as 1.0). Target cDNA was amplified using Qiagen Dr_atp2b4_1SG QuantiTect primer assay and Platinum SYBR Green qPCR super-Mix-UDG. Standard cycling conditions were run with a Step-One-Plus real time PCR system (Applied Biosystems), and the resulting Ct values analyzed using the 2-ΔΔCT method.

In Vitro Model of Cisplatin Toxicity

HK-2 cells (human proximal tubular line) obtained from ATTC (Manassas, Va., USA) were cultured in DMEM/F12 supplemented with glutamine, 10% FBS and antibiotics, and were maintained at 37° C. in 5% $CO_2$. Cells were exposed to cisplatin (20 μM) in the presence or absence of recombinant renalase or renalase peptides for 24 hrs, and cell viability was assessed by the WST1 method (Roche Applied Science, Germany).

To examine renalase dependent MAPKs signaling, cells treated with RP-220 (15 ug/ml) or EGF (100 ng/ml) as a positive control were harvested in RIPA buffer (20 mM Tris-HCl, pH 7.5, 150 mM NaCl, 1 mM $Na_2EDTA$, 1 mM EGTA, 1% NP-40, 1% sodium deoxycholate, 2.5 mM sodium pyrophosphate, 1 mM α-glycerophosphate, 1 mM $Na_3VO_4$, 1 μg/ml leupeptin) supplemented with a protease and phosphatase inhibitor cocktail (Roche Applied Science, Germany). Proteins were separated by SDS-PAGE and immunoblotting was carried out using the following antibodies: anti-renalase monoclonal antibodies (Desir et al., 2012, J. Am. Heart Assoc. 1:e002634; Lee et al., 2013, J. Am. Soc. Nephrol. 24:445-455), and antibodies specific for total and phosphorylated ERK, p38, and JNK (Cell Signaling Technology, MA, USA). The following inhibitors were obtained from Sigma-Aldrich Corp (St. Louis, Mo.): U0126 (1,4-diamino-2,3-dicyano-1,4-bis[2-aminophenylthio]) for ERK1/2, and SB203580 (4-[4'-Fluorophenyl]-2-[4'-methyl-sulfinylphenyl]-5-[4'-pyridyl]-imidazole) for p38 α-β.

Statistical Analysis

When appropriate, the Kruskal-Wallis one-way analysis of variance by ranks was used to evaluate statistical significance. When the Kruskal-Wallis test revealed statistical significance, the Mann-Whitney test was used for pairwise comparisons. All data are mean±SEM, and values of $P<0.05$ were accepted as a statistically significant difference. Statistical analysis was carried out using GraphPad Prism (GraphPad Software, Inc.).

The results of the experiments are now described.

Protection by RP-220 Against Cisplatin Toxicity Linked to p38 MAPK Activation

It has previously been shown that in renalase KO mice, renalase deficiency worsens ischemic AKI, while the administration of recombinant renalase significantly attenuates AKI (Lee et al., 2013, J. Am. Soc. Nephrol. 24:445-455). Additional studies indicate that the protective effect of renalase against ischemic and cisplatin AKI does not depend on the enzymatic activity of renalase, but rather is mediated by the interaction of renalase or short renalase peptides (RP-224, RP-220 and RP-H220, FIG. 1a) with a receptor(s). A scrambled renalase peptide, RP-Scr220, did not activate MAPK signaling, and failed to protect cells (Wang et al., 2014, J. Am. Soc. Nephrol. DOI:10.1681/asn.2013060665). The protective effects of renalase peptides corresponded to the activation of intracellular signaling that promotes cell survival (Wang et al., 2014, J. Am. Soc. Nephrol. DOI: 10.1681/asn.2013060665).

Figure 1C:
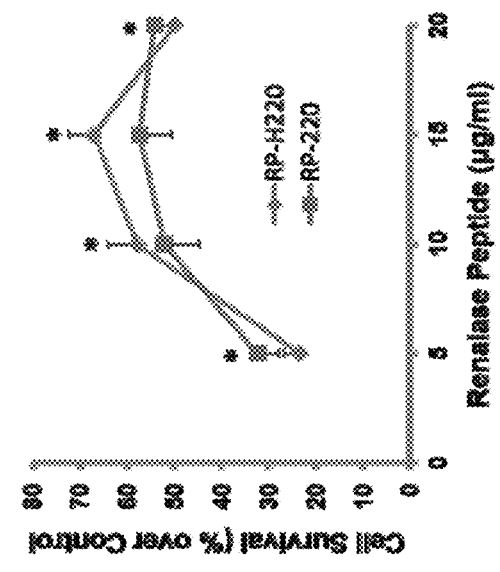
Figure 1B:
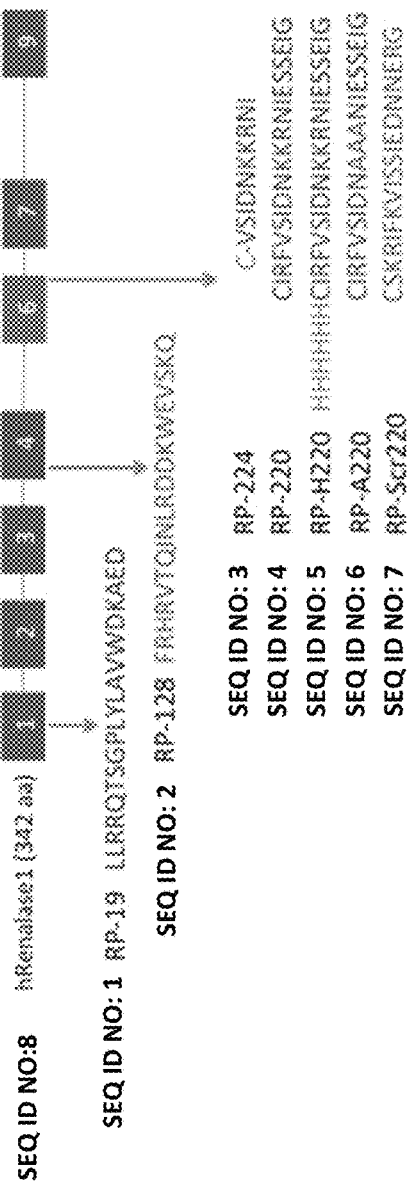
Figure 1D:
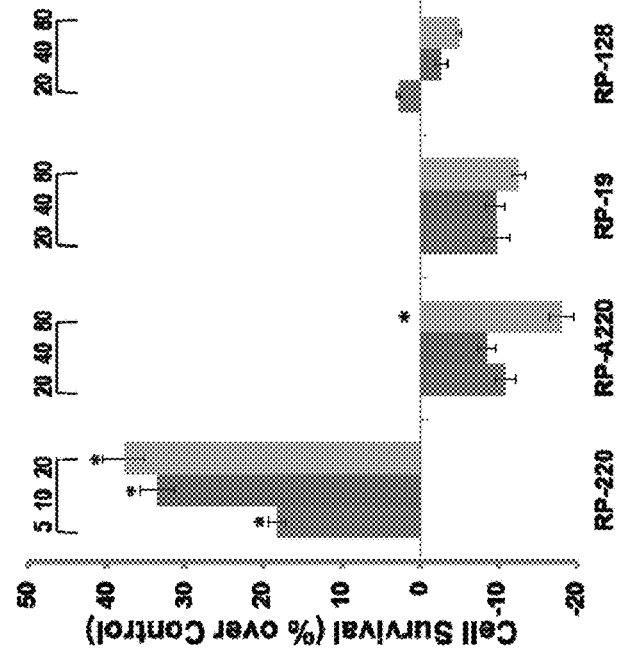

In order to determine if RP-220 could be used as probe to identify the receptor(s) for extracellular renalase, its specificity was examined by comparing its protective effect against cisplatin toxicity to that of mutated RP-220 (RP-A220; SEQ ID NO: 6), and of renalase peptides RP-19 (SEQ ID NO: 1) and RP-128 (SEQ ID NO: 2; FIG. 1A). Renalase peptides RP-19 and RP-128 were chosen because they contain putative ERK docking (D) domains (Motif Scan) (Roux and Blenis, 2004, Microbiol. Mol. Biol. Rev. 68:320-344). RP-220 significantly protected HK-2 cells exposed to cisplatin for 24 hrs in a dose dependent manner (FIG. 1B). Control peptides RP-19, RP-128, and RP-A220 did not improve cell survival, and at the highest concentration (80 μg/ml), RP-A220 actually exacerbated cisplatin toxicity. Recombinant renalase (80 μg/ml), RP-224 (100 μg/ml), RP-220 (15 μg/ml), and RP-H220 (15 μg/ml) protected HK-2 cells to a similar degree (FIG. 1C). The concentration dependent effects for RP-220 and RP-H220 indicated that both peptides are equipotent at protecting HK-2 cells against cisplatin cytotoxicity, and RP-220 (15 μg/ml) was used for all subsequent studies (FIG. 1D).

Figure 2C:
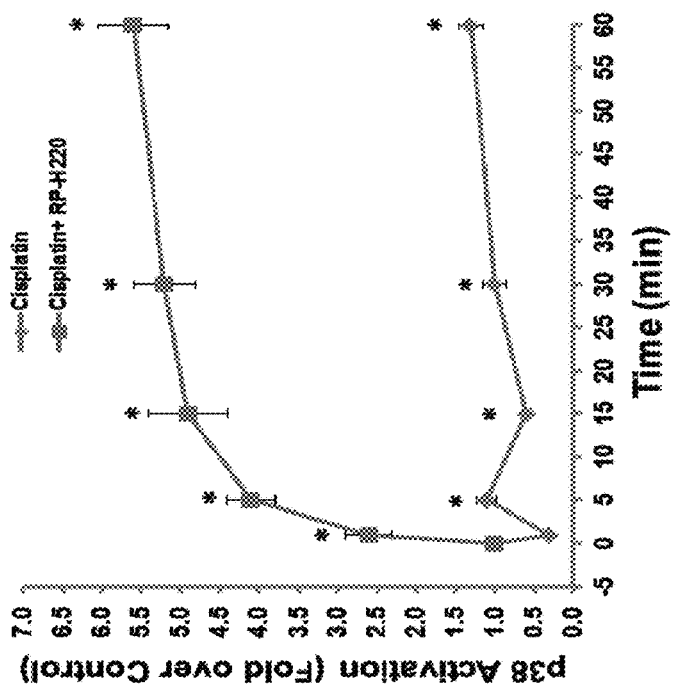
FIGS. 2A-2C, depict how RP-220 alters the pattern of MAPK activation in cisplatin treated cells.
Figure 2A:
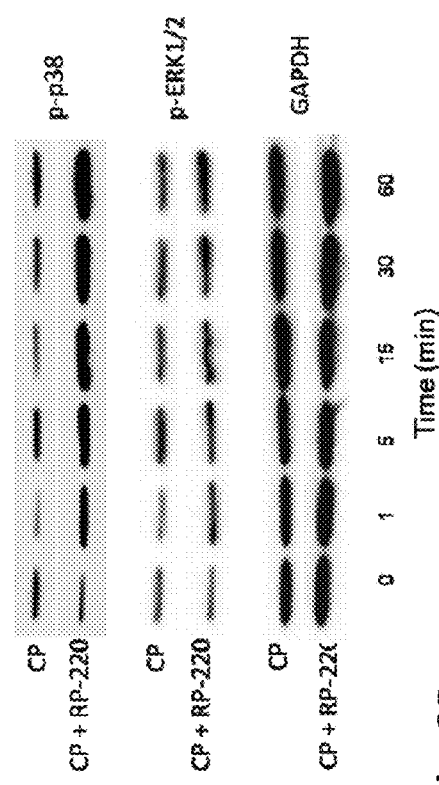
Figure 2B:
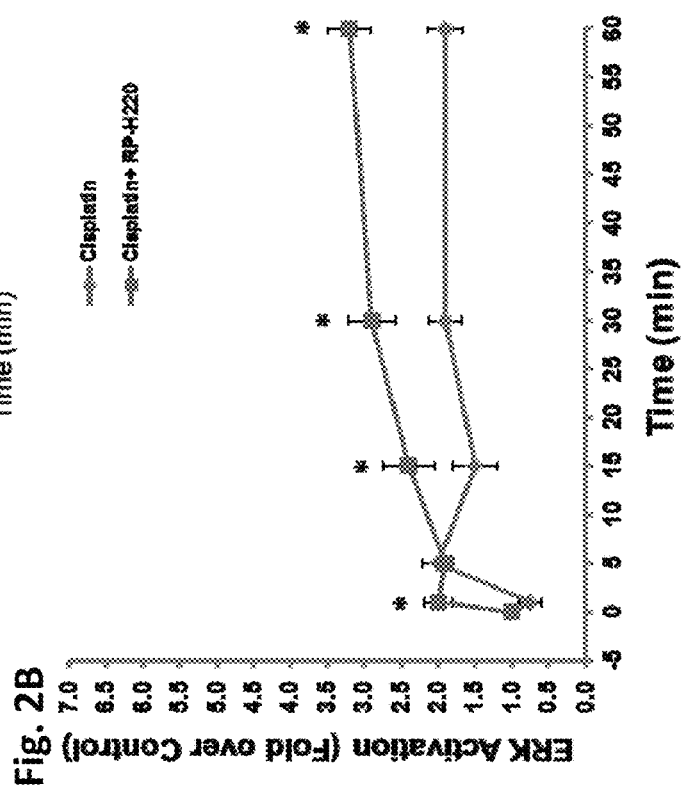

It has previously been demonstrated that both Renalase1 and RP-220 treatments rapidly increased ERK and p38 phosphorylation in HK-2 cell (Wang et al., 2014, J. Am. Soc. Nephrol. DOI:10.1681/asn.2013060665). To test if protection of HK-2 cells against cisplatin toxicity by RP-220 was linked to MAPK activation, the patterns of MAPK signaling were examined at early time points (1-60 min) in HK-2 cells exposed to cisplatin with and without RP-220. Cisplatin alone modestly increased ERK and p38 phosphorylation (FIGS. 2A-2C). This effect on p38 phosphorylation was markedly enhanced (5 fold) by the addition of RP-220 (FIG. 2C). However, only a slight increase in ERK activation (0.5 fold) was noted with RP-220 over that elicited by cisplatin alone (FIG. 2B). Although not wishing to be bound to any particular theory, these results suggest that RP-220's cytoprotective action may be due to its activation of p38 and not ERK.

Figure 3B:
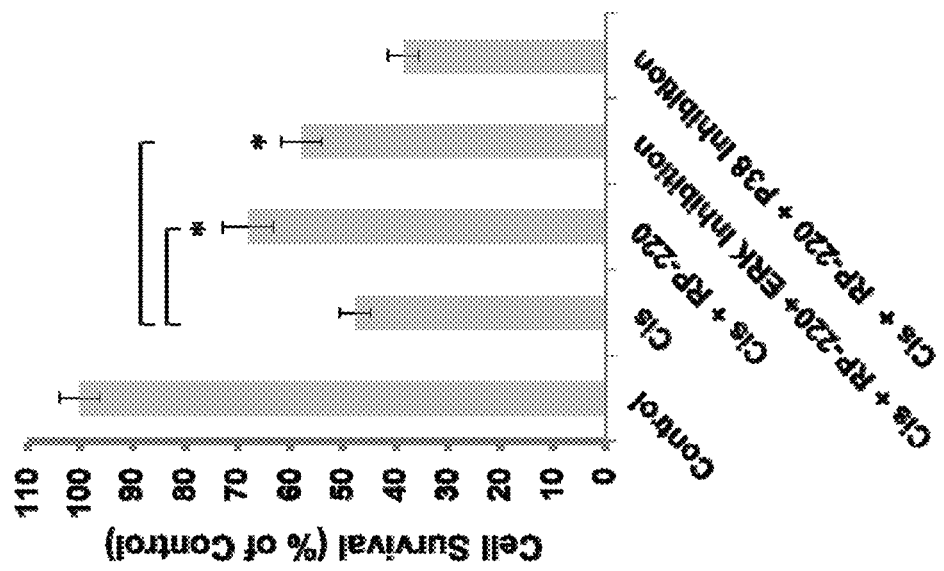
FIGS. 3A-3B, depict how the inhibition of p38 abrogates the protective effect of RP-220.
Figure 3A:
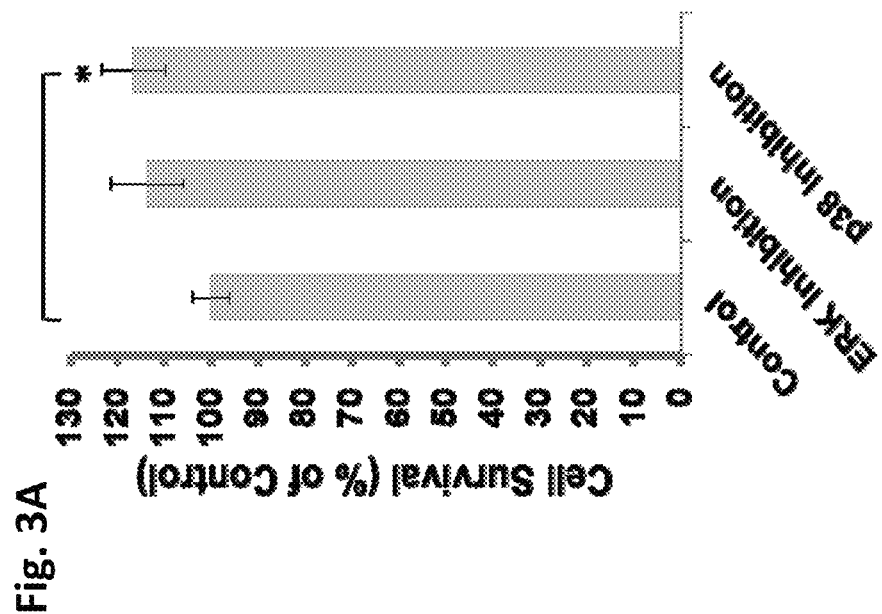

To determine the relative importance of ERK and p38 as mediators of RP-220's protective effect, their activities were chemically inhibited. Reducing the activity of ERK1/2 (U0126), or p38α-β (SB203580) was examined in HK-2 cells under control conditions. In control studies, ERK and p38 inhibition had no deleterious effect and were not found to reduce HK-2 cell survival (FIG. 3A). In HK-2 cells treated with both cisplatin and RP-220, ERK inhibition did not diminish the protection conferred by RP-H220 (FIG. 3B). In marked contrast, p38 inhibition completely abrogated the RP-220's protection (FIG. 3B). This result provides strong support for the hypothesis that p38 is a key mediator of RP-220's defense against cisplatin toxicity.

Figure 4A:
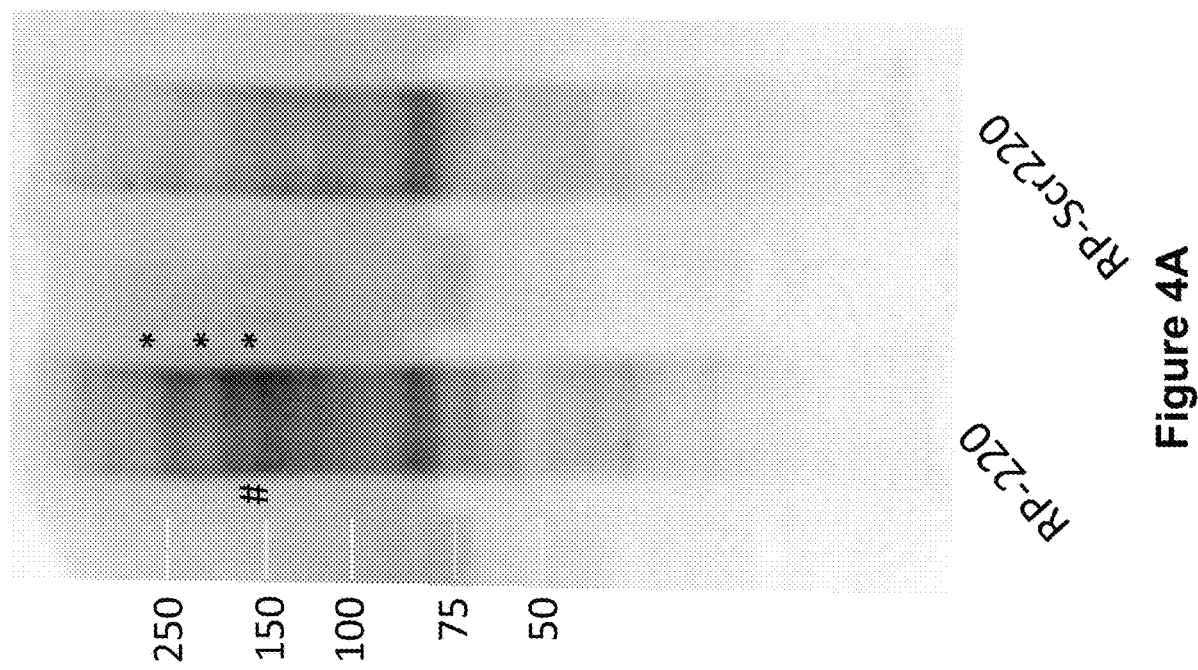

Extracellular Renalase Binds to the Plasma Membrane $Ca^{++}$-ATPase Isoform PMCA4b RP-220 was used as a probe to identify a plasma membrane protein(s) that interact with extracellular renalase. The biotin label transfer method was used with the label transfer reagent Mts-Atf-Biotin, which was linked to the single cysteine located at the N terminus of RP-220. Labeled RP-220 was incubated with HK-2 cells for 24 hrs at 4° C. to minimize internalization, and was cross-linked to the interacting protein(s) by exposure to UV light. The biotin-labeled proteins were purified using a streptavidin column and identified by mass spectrometry. The plasma membrane calcium-ATPase isoform, PMCA4b, was reproducibly cross-linked to RP-220 (FIG. 4A). PMCA4b was abundantly expressed in HK-2 cells (FIG. 4B) and co-localized with renalase at the plasma membrane (arrows), and within the cytoplasm of HK-2 cells (FIG. 4C).

In vitro interaction between endogenously expressed PMCA4b and RP-220 was evaluated by co-immunoprecipitation. Agarose beads coated with either PMCA4b or renalase antibody depleted whole cell lysates of renalase (FIG. 4D, upper blot, lanes 1 vs 2 and 3), and renalase could be eluted from both sets of beads (FIG. 4D, upper blot, lanes 4-5). The blot was re-probed with an anti-PMCA4b antibody, and likewise, PMCA4b could be eluted from both sets of beads (FIG. 4D, bottom blot, lanes 4-5). Of note, endogenous expression of PMCA4b is significantly higher than that of renalase (FIG. 4D, upper and lower blots, lanes 1), and as a consequence less PMCA4b protein is eluted from beads coated with the renalase antibody than from those coated with the PMCA4b antibody. (FIG. 4D, upper and lower blots, lanes 4 vs 5). In addition, PMCA4b coated beads completely depleted renalase from the supernatant. Although not wishing to be bound to any particular theory, this result suggests that extracellular renalase is largely bound to PMCA4b.

PMCA4b Mediates Renalase's Action on Cell Signaling and Cytoprotection

Figure 5A:
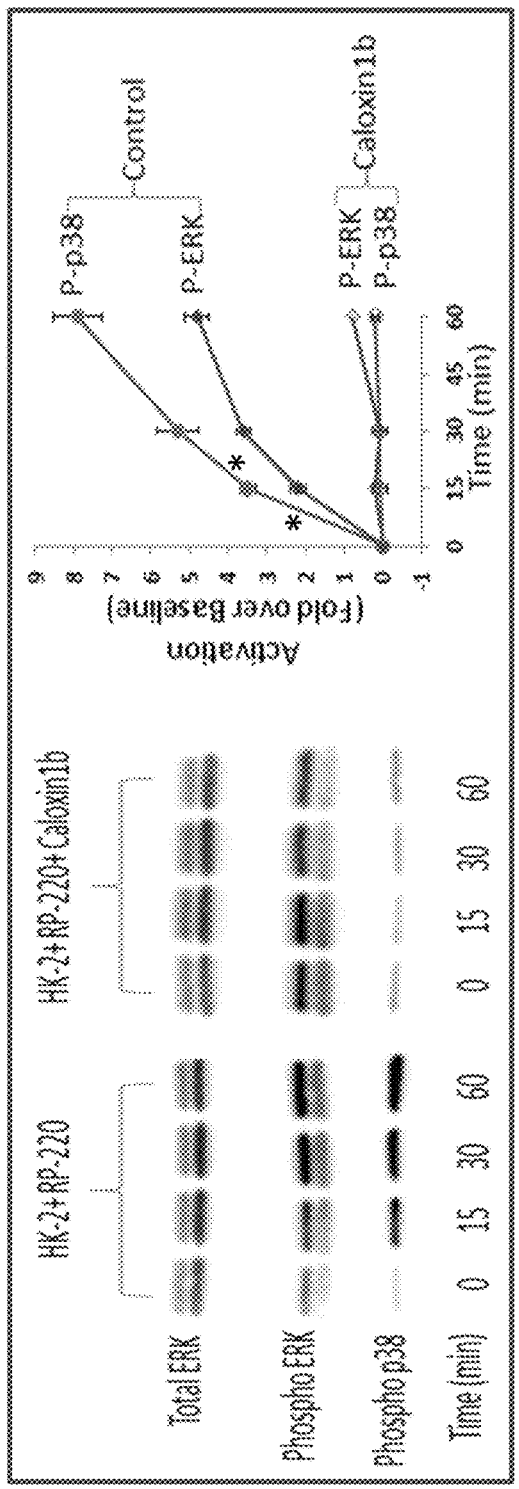
FIGS. 5A-5E, depict how PMCA4b inhibition abrogates renalase peptide mediated MAPK signaling and cytoprotection.
Figure 5B:
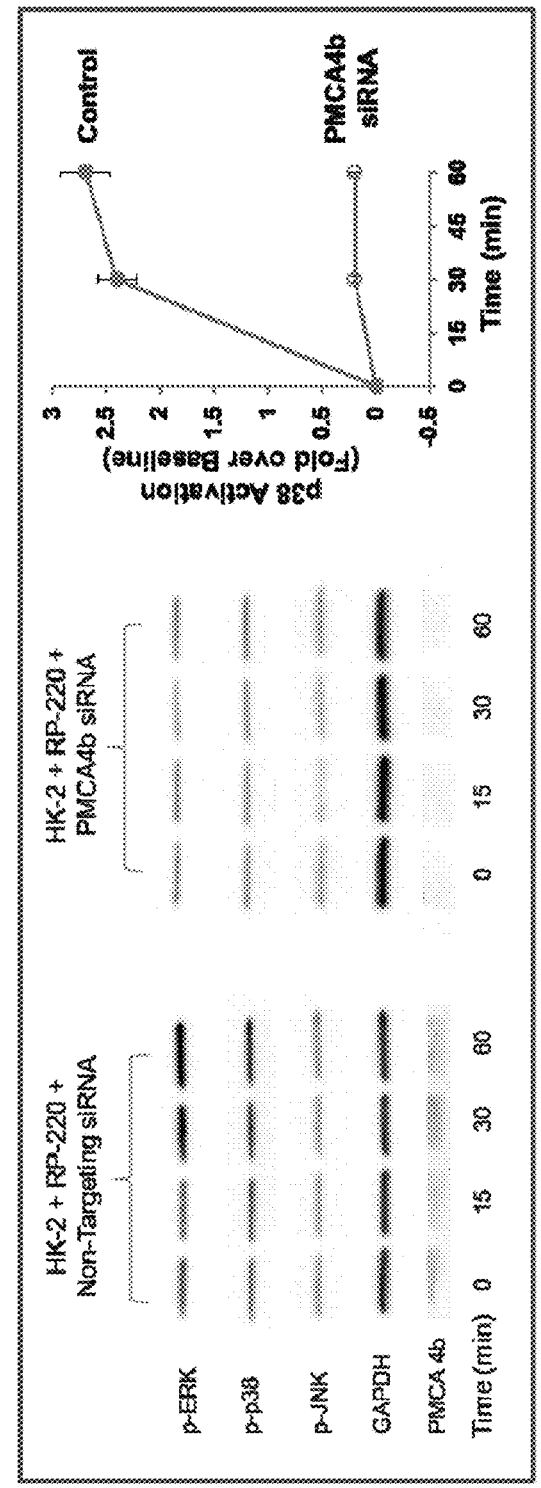
Figure 5C:
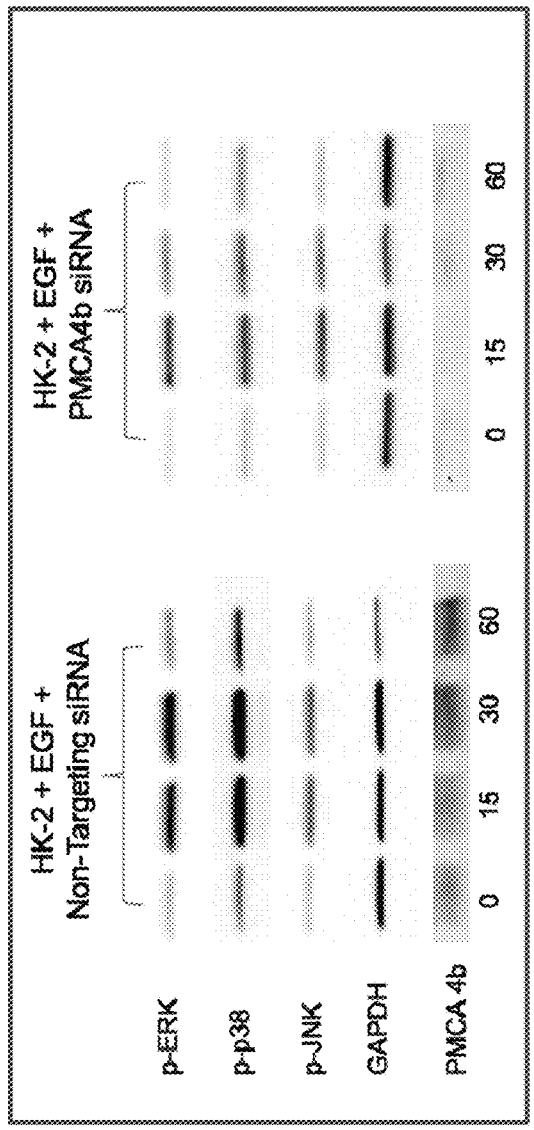

It was next determined whether inhibition of PMCA4b activity modulated renalase mediated MAPK signaling. Caloxin1b, a peptide inhibitor of PMCA4b (Pande et al., 2008, J. Cell. Mol. Med. 12:1049-1060, abrogated renalase-mediated ERK and p38 MAPKs phosphorylation in HK-2 cells (FIG. 5A). Since Caloxin1b is reported to also inhibit PMCA1, additional evidence regarding PMCA4b's role in renalase mediated signaling was obtained by specifically down-regulating PMCA4b expression using siRNA. In control studies, non-targeting siRNAs affected neither PMCA4b expression nor RP-220 mediated p38 (FIG. 5B, left panel). In contrast, PMCA4b-targeting siRNAs decreased protein expression by more than 90% and prevented RP-220 mediated p38 phosphorylation (FIG. 5B, middle and right panels). The specificity of the interaction between RP-220 and PMCA4b was examined by testing if PMCA4b downregulation also affected epidermal growth factor (EGF) mediated MAPK activation. As shown in FIG. 5C, inhibition of PMCA4b expression had no effect on EGF dependent ERK, p38 and JNK phosphorylation.

Figure 5D:
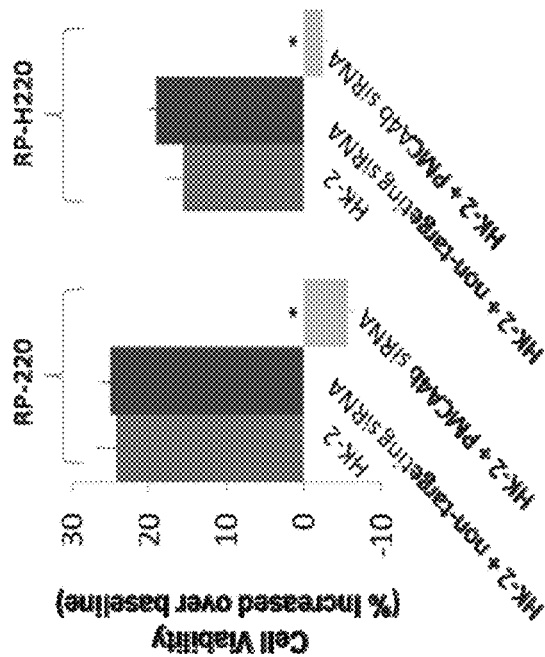
Figure 5E:
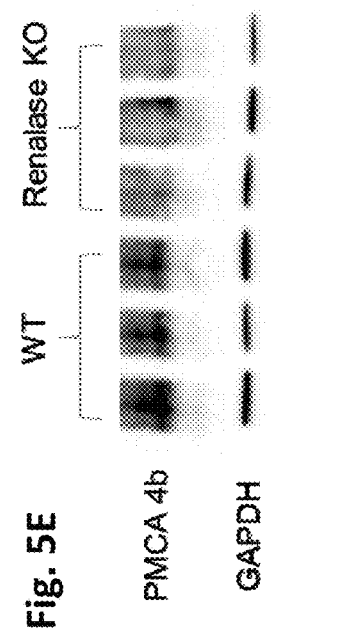

Down-regulation of PMCA4b expression abrogated the protective effect of RP-220 and RP-H220 against cisplatin cytotoxicity (FIG. 5d). It has previously been shown that in marked contrast to what is observed in WT mice, neither renalase nor RP-220 is effective at activating MAPK signaling and at protecting renalase KO mice against mild or severe ischemic AKI (Wang et al., 2014, J. Am. Soc. Nephrol. DOI:10.1681/asn.2013060665). Based on these results, it was hypothesized that the interaction of RP-220 with its cognate receptor was disrupted in the renalase KO, perhaps due to a decrease in receptor gene or protein expression brought about by deletion of the renalase gene. PMCA4b gene expression in the renalase KO mouse was measured by quantitative PCR, and found to be 11.4 fold lower than in WT control (n=6, p<0.03). Expression of PMCA4b protein in WT and renalase KO kidneys was evaluated by western immunoblotting. As shown in FIG. 5E (representative blot), PMCA4b expression in the renalase KO was 63.5±7.5% lower than in WT (n=6, p<0.03). These data provide strong support for the hypothesis that PMCA4b functions as a renalase receptor, and is critical in mediating the signaling and cytoprotective effects of renalase.

Renalase Polypeptide and Peptide Sequences

RP 19-
(SEQ ID NO: 1)
LLRRQTSGPLYLAVWDKAED

RP 128-
(SEQ ID NO: 2)
FRHRVTQINLRDDKWEVSKQ

RP 224-
(SEQ ID NO: 3)
CVSIDNKKRNI

RP 220-
(SEQ ID NO: 4)
CIRFVSIDNKKRNIESSEIG

RP H220-
(SEQ ID NO: 5)
HHHHHHCIRFVSIDNKKRNIESSEIG

RP A220-
(SEQ ID NO: 6)
IRFVSIDNAAANIESSEIG

RP 220 SCRAMBLED-
(SEQ ID NO: 7)
CSKRIFKVISSIEDNNERG

Renalase (NP_001026879.2)-
(SEQ ID NO: 8)
MAQVLIVGAGMTGSLCAALLRRQTSGPLYLAVWDKAEDSGGRMTTACSPH

NPQCTADLGAQYITCTPHYAKKHQRFYDELLAYGVLRPLSSPIEGMVMKE

GDCNFVAPQGISSIIKHYLKESGAEVYFRHRVTQINLRDDKWEVSKQTGS

PEQFDLIVLTMPVPEILQLQGDITTLISECQRQQLEAVSYSSRYALGLFY

EAGTKIDVPWAGQYITSNPCIRFVSIDNKKRNIESSEIGPSLVIHTTVPF

GVTYLEHSIEDVQELVFQQLENILPGLPQPIATKCQKWRHSQVTNAAANC

PGQMTLHHKPFLACGGDGFTQSNFDGCITSALCVLEALKNYI

Renalase (NP_060833.1)-
(SEQ ID NO: 9)
MAQVLIVGAGMTGSLCAALLRRQTSGPLYLAVWDKAEDSGGRMTTACSPH

NPQCTADLGAQYITCTPHYAKKHQRFYDELLAYGVLRPLSSPIEGMVMKE

GDCNFVAPQGISSIIKHYLKESGAEVYFRHRVTQINLRDDKWEVSKQTGS

PEQFDLIVLTMPVPEILQLQGDITTLISECQRQQLEAVSYSSRYALGLFY

EAGTKIDVPWAGQYITSNPCIRFVSIDNKKRNIESSEIGPSLVIHTTVPF

GVTYLEHSIEDVQELVFQQLENILPGLPQPIATKCQKWRHSQVPSAGVIL

GCAKSPWMMAIGFPI

Example 2: Modulation of the Activity of PMCA4b Mediates Renalase's Cytprotective Action The effect of renalase on the ATPase activity of PMCA4b is examined, including its effect on Vmax, Km, and constitutive activation. The local and/or global effect of renalase's interaction with PMCA4b on calcium dynamics is also examined. Whether the disruption of the PMCA4b macromolecular complex with RAS SF-1 modulates the action of renalase (MAPK signaling and cytoprotection) is further examined. Whether PMCA4b knockout mice respond differently than wild type mice to renal ischemia or exposure to cisplatin is examined, as is whether renalase modifies the extent of renal injury.

Example 3: Assessment of Renalase in Pancreatitis

As described elsewhere herein, the region of renalase that affects pancreatitis and cell signaling responses has been isolated in a region of the molecule that lacks enzyme activity. The peptide containing this activity, RP-220, is conserved in all renalase isoforms, but lacks the amine oxidase activity of recombinant renalase and instead acts only as a signaling molecule. In the studies described herein, renalase is administered as both a recombinant full-length human renalase or as the 20 amino acid peptide (RP-220). RP-220 dramatically decreases inflammatory, ischemic acute kidney injury in WT mice independent of its enzymatic activity.

Cytosolic $Ca^{2+}$ Signaling Mediates Pancreatitis

The acinar events that lead to pancreatitis are $Ca^{2+}$-dependent, associated with pathologic cytoplasmic calcium signaling, and can be modified by the plasma membrane $Ca^{2+}$ ATPase (PMCA). Under physiologic conditions, coordinated, oscillatory $Ca^{2+}$ signals that originate in the apical region of the acinar cell are linked to the secretion of inactive zymogens from acinar cell into the pancreatic duct (Williams, 2001, Annu Rev Physiol 63, 77-97). In pancreatitis, a different acinar cell $Ca^{2+}$ signaling pattern is observed. Instead of the physiologic increase in oscillations and several-fold increases in cytosolic $Ca^{2+}$, pancreatitis is associated with a global, peak-plateau pattern, with much larger rise in $Ca^{2+}$ followed by a sustained elevation at a lower level (Matozaki et al., 1990, JMV-180. J Biol Chem 265, 6247-6254). Pathologic $Ca^{2+}$ signaling and $Ca^{2+}$ overload have been linked to most of the early events in the pathogenesis of acute pancreatitis, including zymogen activation, inhibition of secretion, inflammation, and necrosis (Raraty et al., 2000, Proc Natl Acad Sci USA 97, 13126-13131; Muallem et al., 1995, J Cell Biol 128, 589-598; Criddle et al., 2006, Gastroenterology 130, 781-793; Gerasimenko et al., 2002, J Cell Sci 115, 485-497; Huang et al., 2013, Gut; Awla et al., 2012, Gastroenterology 143, 1352-1360 e1357).

Physiologic levels of cytosolic acinar cell $Ca^{2+}$ are maintained through the actions of several $Ca^{2+}$ pumps and channels, including the plasma membrane $Ca^{2+}$ ATPase (PMCA). PMCA, which actively pumps $Ca^{2+}$ from the cell, is the main $Ca^{2+}$ efflux pathway in the acinar cell, which lacks functional $Na^+/Ca^{2+}$ exchanger (Tepikin et al., 1992, J Biol Chem 267, 3569-3572; Petersen, 2003, Cell Calcium 33, 337-344). PMCA is a key regulator of baseline $Ca^{2+}$ levels and defender against pathological increases in intracellular $Ca^{2+}$. PMCA exists in four isoforms. PMCA1 and PMCA4 are ubiquitously expressed, while PMCA2 and PMCA3 are tissue specific and expressed mainly in neurons (Lopreiato et al., 2014, J Biol Chem 289, 10261-10268). PMCA is activated by calmodulin (Falchetto et al., 1992, Protein Sci 1, 1613-1621) and regulated through phosphorylation by several protein kinases (Wang et al., 1991, J Biol Chem 266, 9078-9085; Smallwood et al., 1988, J Biol Chem 263, 2195-2202; James et al., 1989, Biochemistry 28, 4253-4258). Inhibition of PMCA in acinar cells inhibits $Ca^{2+}$ efflux induced by supramaximal acetylcholine and worsens antioxidant-induced necrosis in acinar cells in vitro (Ferdek et al., 2012, Curr Biol 22, 1241-1246). Additionally, the protective effects of insulin on pancreatitis responses are mediated by its ability to preserve PMCA activity and prevent pathological increases in $Ca^{2+}$ (Samad et al., 2014, J Biol Chem 289, 23582-23595; Mankad et al., 2012, J Biol Chem 287, 1823-1836).

These observations are consistent with the explanation that PMCA is a key mediator of $Ca^{2+}$ extrusion from the acinar cell and reduces cell injury by lowering cytoplasmic $Ca^{2+}$ levels.

Figure 6A:
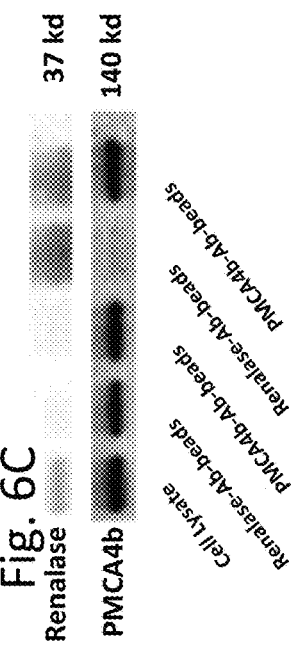
FIGS. 6A-6D, depict the results of experiments showing a plasma membrane calcium ATPase is a receptor the secretory protein renalase and appears to mediate the cytoprotective effects of renalase.
Figure 6B:
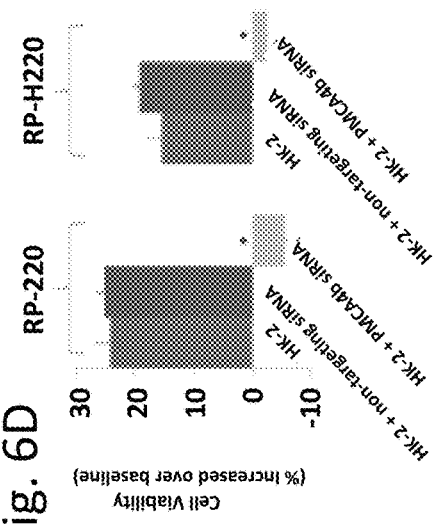
Figure 6C:
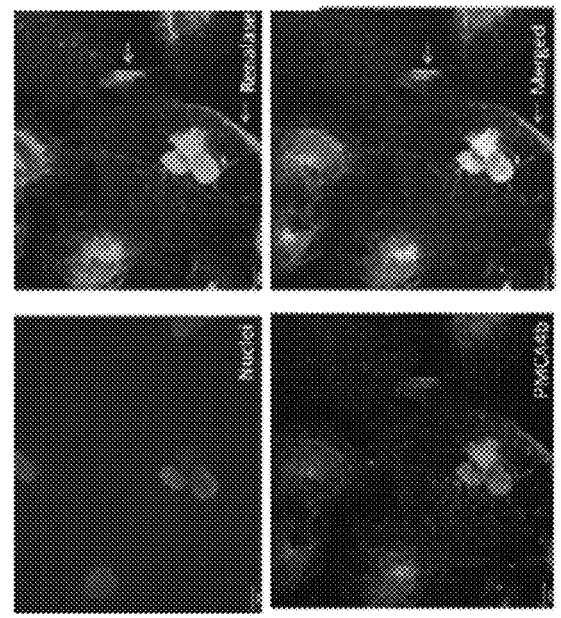
Figure 6D:
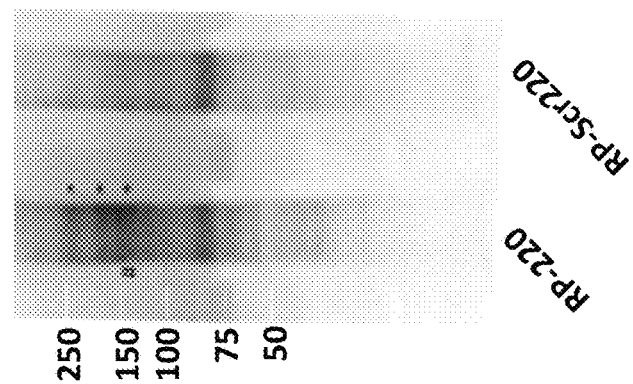

The plasma membrane $Ca^{2+}$ ATPase (PMCA) is the receptor for renalase (Wang et al., 2015, Identification of a Receptor for Extracellular Renalase. PLoS ONE 10, e0122932). As described elsewhere herein, the protective effects of renalase exhibit saturable kinetics, consistent with the explanation that it acts through a plasma membrane receptor. Affinity crosslinking of a biotinylated renalase peptide (RP-220) to membrane proteins in human proximal tubular cell line (HK-2) and protein identification by mass spectrometry identified the PMCA4b as the major renalase binding protein (FIG. 6A). Co-localization (FIG. 6B) and co-immunopreceipitation (FIG. 6C) confirmed protein-protein interaction between endogenous renalase and PMCA4b. PMCA4b is a widely expressed plasma-membrane $Ca^{2+}$ extruder that is localized to the basolateral membrane of polarized cells (Antalffy et al., 2012, Cell Calcium 51, 171-178; Lopreiato et al., 2014, J Biol Chem 289, 10261-10268). The data described herein are consistent with the explanation that renalase activates PMCA to decrease cytoplasmic $Ca^{2+}$ levels (FIGS. 12 and 13). Additionally, FIG. 6D shows that down-regulation of endogenous PMCA4b expression by siRNA transfection blocks the protective effects of RP-220 in HK-2 cells.

Renalase is Present in Mouse Acinar Cells and its Levels are Reduced in the Serum after Inducing Acute Experimental Pancreatitis FIGS. 7A and 7B show that renalase is expressed in the pancreatic acinar cell, but at lower levels than the kidney. Since renalase is present in the serum (FIG. 6C), renalase could affect the acinar cells through autocrine/paracrine pathways and also as a hormone. Serum renalase levels decrease in a time-dependent manner in mice after initiating cerulein-induced pancreatitis, falling by about 70% after 7 hrs of cerulein pancreatitis (FIG. 7C). These observations have important implications: i) the protective effects of serum renalase are lost during the onset of acute pancreatitis and ii) renalase is useful as a disease biomarker.

Genetic Deletion of Renalase Leads to Worsening of Acute Pancreatitis

Since renalase has a protective effect, the genetic deletion of endogenous renalase is associated with greater injury. This issue was examined in mice with genetic deletion of renalase. FIG. 7B shows the loss of renalase protein in the knockout mouse. Though the knockouts (renalase −/−) breed slowly and have slight elevations in their resting blood pressure, they have no other overt phenotype. FIG. 8 shows that renalase knockout (−/−) mice exhibit more severe cerulein-induced pancreatitis, as measured by zymogen activation, edema, and histologic severity than wild-type (WT). This finding is consistent with the explanation that endogenous renalase has a protective effect in acute pancreatitis. Thus, a reduction in renalase levels at the onset of acute pancreatitis may increase disease severity.

Renalase Reduces Injury in Pancreatic Acini

Next, it was assessed whether pretreatment with recombinant human renalase reduces injury in pancreatitis. This was first assessed in isolated groups of murine acinar cells (acini) that were exposed to supraphysiologic concentrations of cerulein and carbachol (which induces early acinar cell pancreatitis responses) in isolated WT mouse acini and acini isolated from renalase deficient mice in vitro (FIG. 9). The recombinant renalase reduced trypsinogen activation induced by either cerulein (FIG. 9A) or carbachol (FIG. 9B). Acini from renalase knockout (KO) mice also showed reduced trypsinogen activation after renalase addition (FIG. 9C). Renalase had no effect on untreated acini or acini treated with physiologic stimulation. Recombinant full-length renalase and the truncated renalase peptide (RP-220) showed similar potency in protecting acini from injury.

Pre-Treatment with Exogenous Recombinant Renalase Decreased Symptoms of Pancreatitis Injury In Vitro (Acini) and In Vivo To determine whether the protective of renalase observed in isolated acini was relevant in vivo, WT mice were pretreated (1 hour) with a single dose of the renalase peptide (RP-220) intraperitoneally (100 µg peptide/25 g body weight) prior to inducing cerulein-pancreatitis (6 hourly injections IP of 50 µg/kg). This prophylactic pretreatment reduced all measures of pancreatitis severity including, zymogen activation, edema, apoptosis, inflammatory cell infiltrate, and histologic severity 7 hours after inducing disease (FIG. 10). Next, we examined whether giving renalase after disease onset could reduce disease severity.

Figure 11:
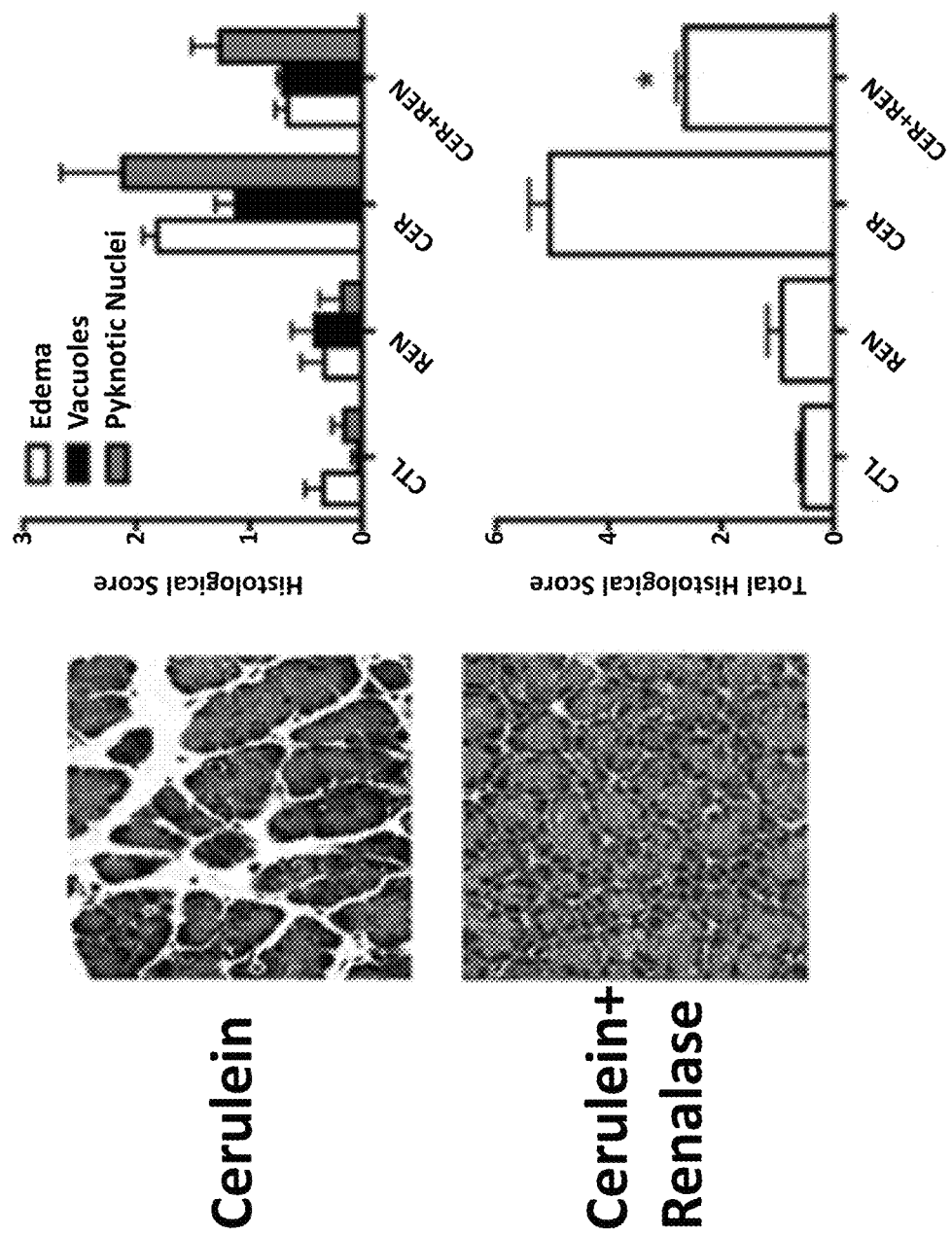
FIG. 11 depicts the results of experiments showing that treatment with renalase 2 hours after the onset of cerulein pancreatitis significantly reduces injury. A single dose of renalase was given intraperitoneally (100 µg peptide/25 g body weight) 2 hours after inducing cerulein-pancreatitis. Six hourly injections IP of 50 µg/kg and animals were sacrificed at hour 7. Histologic pancreatitis severity was evaluated by two blinded reviewers. This therapeutic treatment decreased pancreatitis in each category and the total histologic scores (bottom graph) was significantly less in the renalase treated cerulein (CER) vs. CER alone. *$p<0.05$ Wilcoxon rank sum. N=4 mice in each group.

Post-Treatment with Exogenous Recombinant Renalase after the Onset of In Vivo Pancreatitis Reduced Symptoms of Injury The same protocol was used as in the experiments in FIG. 10 to induce cerulein pancreatitis in WT mice, but renalase was not given until 2 hours after initiating disease (FIG. 11). Individual and aggregate histologic scores demonstrated that renalase significantly decreased injury. The data shown in FIG. 10 and FIG. 11 indicate that exogenous renalase can reduce the severity of pancreatitis in both a prophylactic and therapeutic context.

Exogenous Renalase Affects Cytosolic $Ca^{2+}$ Signaling and Appears to Activate the Plasma Membrane $Ca^{2+}$ ATPase (PMCA)

PMCA selectively binds renalase (FIG. 6). To determine if renalase affects the activity of PMCA4b (FIG. 6), an important mediator of $Ca^{2+}$ extrusion in many cell types, renalase effects on $Ca^{2+}$ extrusion were examined. Since the protective effects of renalase were first characterized in HK-2 cells (human kidney cell line) (Lee et al., 2013, J Am Soc Nephrol 24, 445-455; Wang et al., 2014, Journal of the American Society of Nephrology: JASN), its effects on $Ca^{2+}$ signals were evaluated in these cells and subsequently in mouse acinar cells (FIG. 12). Renalase did not change baseline $Ca^{2+}$ levels in either cell type. To isolate effects on $Ca^{2+}$ efflux through PMCA, other $Ca^{2+}$ channels/pumps were blocked so that changes in cytosolic $Ca^{2+}$ were solely due to PMCA. This included inhibition of re-uptake into the endoplasmic reticulum and, in the case of HK2 cells, inhibition of the plasma-membrane $Na-Ca^{2+}$ exchanger that, similar to PMCA, extrudes $Ca^{2+}$ but is not present in acinar cells. To prevent $Ca^{2+}$ influx after stimulation, cells were perfused with $Ca^{2+}$ free medium with 1 mM EDTA. Cells were also pretreated with cyclopiazonic acid to deplete ER stores. To inhibit the $Na^+/Ca^{2+}$ exchangers present in HK2 cells, but not acinar cells (Muallem et al., 1988, J Membr Biol 102, 153-162), $Na^+$-free medium was used in HK2 cells (but not in acinar cells). HK2 cells and isolated mouse acini were perfused with $Ca^{2+}$-free medium and then briefly stimulated with 10 nM angiotensin IV (HK2 cells) or 100 nM cerulein (acinar cells) in the presence of 1.3 mM $Ca^{2+}$ to increase intracellular $Ca^{2+}$. Perfusion buffer was then switched back to $Ca^{2+}$-free medium in the presence or absence of renalase, and cytosolic $Ca^{2+}$ levels were monitored over time and the rates of $Ca^{2+}$ efflux were calculated (FIG. 12). In both HK2 cells and acinar cells, renalase increased the rate of $Ca^{2+}$ efflux.

Since PMCA has been identified as a renalase receptor and renalase enhances $Ca^{2+}$ efflux, it was assessed whether PMCA inhibition would block the protective effects of renalase. FIG. 13 shows that pretreatment of acini with caloxin 1b1, a selective peptide inhibitor of PMCA 4b (inhibition of PMCA4b>PMCA1>PMCA2>PMCA3) that binds to its extracellular loops (Strehler et al., 2013, Journal of pharmacy & pharmaceutical sciences: a publication of the Canadian Society for Pharmaceutical Sciences, Societe canadienne des sciences pharmaceutiques 16, 190-206; Pande et al., 2008, Journal of cellular and molecular medicine 12, 1049-1060), eliminated the protective effect of renalase on zymogen activation, cellular injury by MTT and histology. Together (FIG. 6, FIG. 12, FIG. 13), the results described herein are consistent with the explanation that renalase stimulates PMCA and increases the rates of calcium efflux and that this effect is related to the protective effects of renalase on acinar cell injury.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of treating a pancreatic disease or disorder in a subject in need thereof, the method comprising administering to the subject a therapeutically effective amount of a composition comprising a biologically active renalase polypeptide fragment consisting of an amino acid sequence of SEQ ID NO: 4, wherein the pancreatic disease or disorder is selected from the group consisting of acute pancreatitis and chronic pancreatitis.

2. The method of claim 1, wherein the biologically active renalase polypeptide fragment is administered one time.

3. The method of claim 1, wherein the biologically active renalase polypeptide fragment is administered locally, regionally or systemically.